United States Patent [19]

Sugama

[11] Patent Number: 5,844,058
[45] Date of Patent: Dec. 1, 1998

[54] ORGANOSILOXANE-GRAFTED NATURAL POLYMER COATINGS

[75] Inventor: Toshifumi Sugama, Wading River, N.Y.

[73] Assignee: Brookhaven Science Associates, Upton, N.Y.

[21] Appl. No.: 767,983

[22] Filed: Dec. 17, 1996

[51] Int. Cl.[6] .............................. C08G 79/00; C04B 9/02; B65B 33/00
[52] U.S. Cl. .......................... 527/300; 536/84; 536/101; 536/111; 536/120; 106/14.5; 427/156; 427/435
[58] Field of Search .............................. 527/300; 536/84, 536/101, 111, 120; 106/14.5; 427/156, 435

[56] References Cited

U.S. PATENT DOCUMENTS

| | | | |
|---|---|---|---|
| 3,556,754 | 1/1971 | Marsden . | |
| 4,129,722 | 12/1978 | Iovine et al. | 536/43 |
| 4,540,777 | 9/1985 | Amort et al. | 536/102 |
| 4,584,280 | 4/1986 | Nanao et al. | 501/80 |
| 4,839,449 | 6/1989 | Billmers et al. | 526/238.2 |
| 4,950,583 | 8/1990 | Brewer et al. | 430/311 |
| 4,973,680 | 11/1990 | Billmers | 536/58 |
| 5,004,791 | 4/1991 | Billmers | 527/300 |
| 5,032,683 | 7/1991 | Dragner et al. | 536/104 |
| 5,110,863 | 5/1992 | Sugama | 524/767 |
| 5,200,237 | 4/1993 | Sugama | 427/380 |
| 5,292,799 | 3/1994 | Naito et al. | 524/783 |
| 5,496,937 | 3/1996 | Okamoto et al. | 536/124 |

FOREIGN PATENT DOCUMENTS

| | | |
|---|---|---|
| 0094924A2 | 5/1983 | European Pat. Off. . |
| 0644204A1 | 5/1994 | European Pat. Off. . |

OTHER PUBLICATIONS

Sugama et al., "Zirconocene–modified Polysiloxane–2–Pyridine Coatings", *Thin Solid Films*, 258, 1995, pp. 174–184.

Sugama, "Pectin Copolymers with Organosiloxane Grafts as Corrosion–Protective Coatings for Aluminum", *REDC Material Letters*, vol. 25, Dec. 1995, pp. 291–299.

Sugama et al., "Polyorganosiloxane–Grafted Potato Starch Coatings for Protecting Alumium from Corrosion", *Thin Solid Films*, vol. 289, Nov. 1996, pp. 39–48.

*Primary Examiner*—Nathan M. Nutter
*Attorney, Agent, or Firm*—Margaret C. Bogosian

[57] ABSTRACT

A new family of polysaccharide graft polymers are provided as corrosion resistant coatings having antimicrobial properties which are useful on light metals such as aluminum, magnesium, zinc, steel and their alloys. Methods of making the polysaccharide graft polymers are also included. The methods of making the polysaccharide graft polymers involve reacting a polysaccharide source with an antimicrobial agent under conditions of hydrolysis-condensation.

12 Claims, 14 Drawing Sheets

ORGANOSILOXANE-GRAFTED NATURAL POLYMER COATINGS

This invention was made with Government support under Contract No. DE-ACO2-76CH00016, between the U.S. Department of Energy and Associated Universities, Inc. The invention also has received support from U.S. Army Research Office Program MIPR-ARO-112-93. The Government has certain rights in the invention.

BACKGROUND OF THE INVENTION

This invention relates to a new family of polysaccharide graft polymers, methods of making and using the graft polymers to provide corrosion resistant coatings having antimicrobial properties. More specifically, the new family of polysaccharide graft polymers is provided by reacting a polysaccharide source with an antimicrobial agent.

Water-soluble or dispersable natural polymers, such as starches and cellulosics, are among the most abundant natural resources on both molecular and weight basis, with about 400 billion tons produced photosynthetically in the United States each year. Worldwide, by the year 2000, it has been estimated that natural polymer products will reach about 2000 million tons. Because sources of natural polymers come from seeds and roots of plants, both renewable and abundant agricultural resources, which are also comparatively inexpensive and relatively stable in quality and price. As a result, using natural polymers as an extender and replacement for synthetic polymers might reduce our dependence on petrochemically-derived products.

The hydroxy structures of natural polymers display an excellent affinity to polar substrates, such as cellulose. Thus, although the major consumer of natural polymers are the paper and food industries, these polymers are also widely applied as coatings for paper, and as adhesives in cellulose-based corrugation board, multiwall bags and foil lamination. In using natural polymers as adhesives, susceptibility of the solution adhesive solution to water is a major drawback which must be overcome. Some improvement of water-resistance can be obtained by incorporating water-soluble polymers, such as polyvinyl alcohol and acetate, and thermosetting resins such as ureaformaldehyde or resourcinol-formaldehyde into natural polymers.

Research has been conducted in the past on organosiloxane-containing polysaccharides and polysaccharide graft polymers. For example, U.S. Pat. Nos. 4,973,680 and 5,004,791 to Billmers disclose organosiloxane-containing polysaccharide derivatives and polysaccharide graft polymers usefull in glass fiber forming size compositions, and paper making, adhesives, paper, textile additives as thickeners, sealants, coatings, binders and films. Billmers discloses polysaccharide graft polymers having the structure of

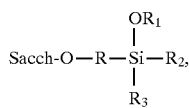

and a polysaccharide graft polymer having the structure Sacch-O—(G)$_n$—(M)$_n$—wherein Sacch- is a polysaccharide; m is 0 or 1; G is the residue of a polymerizable, unsaturated monomer which is bonded to the polysaccharide by an ether or ester linkage; n is greater than 1; and M is the residue of one or more polymerizable, unsaturated, monomer(s), at least one of which is a siloxane-containing monomer, which have been grafted to polysaccharide by free radical polymerization. The polysaccharides disclosed in the '791 and '680 references include starches, gums, cellulose and cellulose derivatives. The organosiloxane compounds used to modify polysaccharides are all trimethoxy or triethoxy silane derivatives.

Several investigators reported that another way to modify starch with synthetic polymers or monomers at molecular level is graft copolymerization in an aqueous or non-aqueous medium. Starch structures were modified through the reaction of the hydroxyl groups with functional groups of synthetic polymers, such as carboxylic acid, anhydride, epoxy, urethane, or oxazoline, and by free-radical ring-opening polymerization occurring between the glucose rings and vinyl monomers.

In the above attempts, it has been found, however, that coatings made of natural polymers such as commercial starch, have many undesirable features. The following characteristics have been found:

(i) microorganisms readily settle and grow on coatings made of natural polymers;

(ii) the coatings have hydrophilic characteristics which form mechanically weak films; and (iii) they also display poor wetting and adhesive properties to metals and other polymer substrates.

Accordingly, there is still a need in the art of coatings for inexpensive, environmentally benign natural polymer coatings which are both corrosion resistant and have antibacterial properties.

It is therefore an object of the present invention to provide chemically modified natural polymer coatings which are inexpensive, environmentally safe and which at the same time strongly adhere to metals such as aluminum, magnesium and zinc, provide anticorrosion protection and cannot be easily attacked by bacteria.

SUMMARY OF THE INVENTION

The present invention, which addresses the needs of the prior art, provides a new family of compounds which are useful as antibacterial corrosion protective coatings for light weight metals such as aluminum, magnesium, zinc, steel and alloys thereof. The new family of compounds include a polysaccharide graft polymer having the structure below

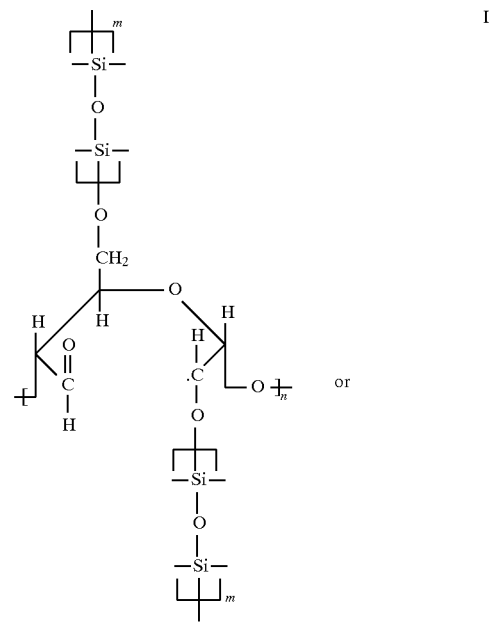

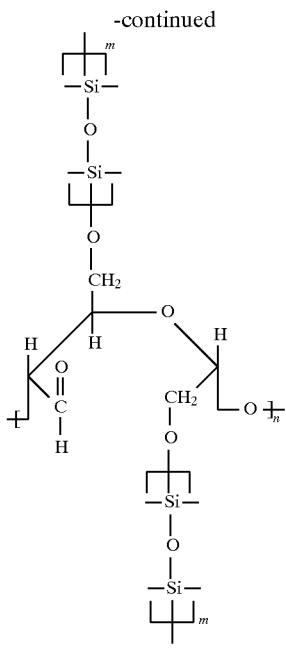
-continued

II wherein m and m are greater or equal to 500. The present invention also provides methods of making the polysaccharide graft polymers of the invention by reacting a polysaccharide source with an antimicrobial agent under conditions of hydrolysis-condensation. The polysaccharide source and the antimicrobial agent are in colloidal aqueous solutions. The hydrolysis-condensation reaction occurs from about 50° C. to about 250° C. The polysaccharide source can be selected from water dispersable commercial starches and cellulosics. Starches include corn, wheat, rice, tapioca, potatoes and sago. Cellulosics include such esters or ethers as cellulose xanthate, methylcellulose, hydroxyethyl cellulose and carboxymethyl-cellulose. Useful antimicrobial agents include N[3-(triethoxysilyl)-propyl]-4,5-dihydroimidazole, β-trimethoxysilylethyl-2-pyridine, β-trimethoxysilylethyl-4-pyridine, 2-[2-trichlorosilyl)ethyl]pyridine, 4-[2-(trichlorosilyl)ethyl]pyridine, N-[3-(triethoxysilyl)propyl]-4-5-dihydroimidazole, 3-bromopropyltrimethoxysilane; 3-iodopropyltrimethoxysilane; (3,3,3-trifluoropropyl)trimethoxysilane; (3,3,3-trifluoropropyl)triethoxysilane; tridecafluoro-1,1,2,2-tetrahydrooctyl-1-triethoxysilane.

As a result of the present invention, a new family of compounds is provided. The compounds are useful as antibacterial corrosion protective coatings for light weight metals. TSPI-modified natural polymer films deposited on aluminum substrates display a superior level of corrosion protection for the substrate. For example, the coatings of the present invention had an impedance of greater than $10^6$ ohm-cm$^2$ after a 20-day exposure to a 0.5N NaCl solution at 25° C., a 1000-hr salt-spray resistance, and a grate protection at both anodic (inhibits pitting) and cathodic sites. The extent of such resistance to corrosion was far better than that of conventional anodic oxide and Cr-conversion coatings. Hence, the modified natural polymer coatings of the present invention have high potential as substitutive material for Cr-incorporating coatings which are also known to be environmentally hazardous.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

DETAILED DESCRIPTION OF THE INVENTION

Figure 1:
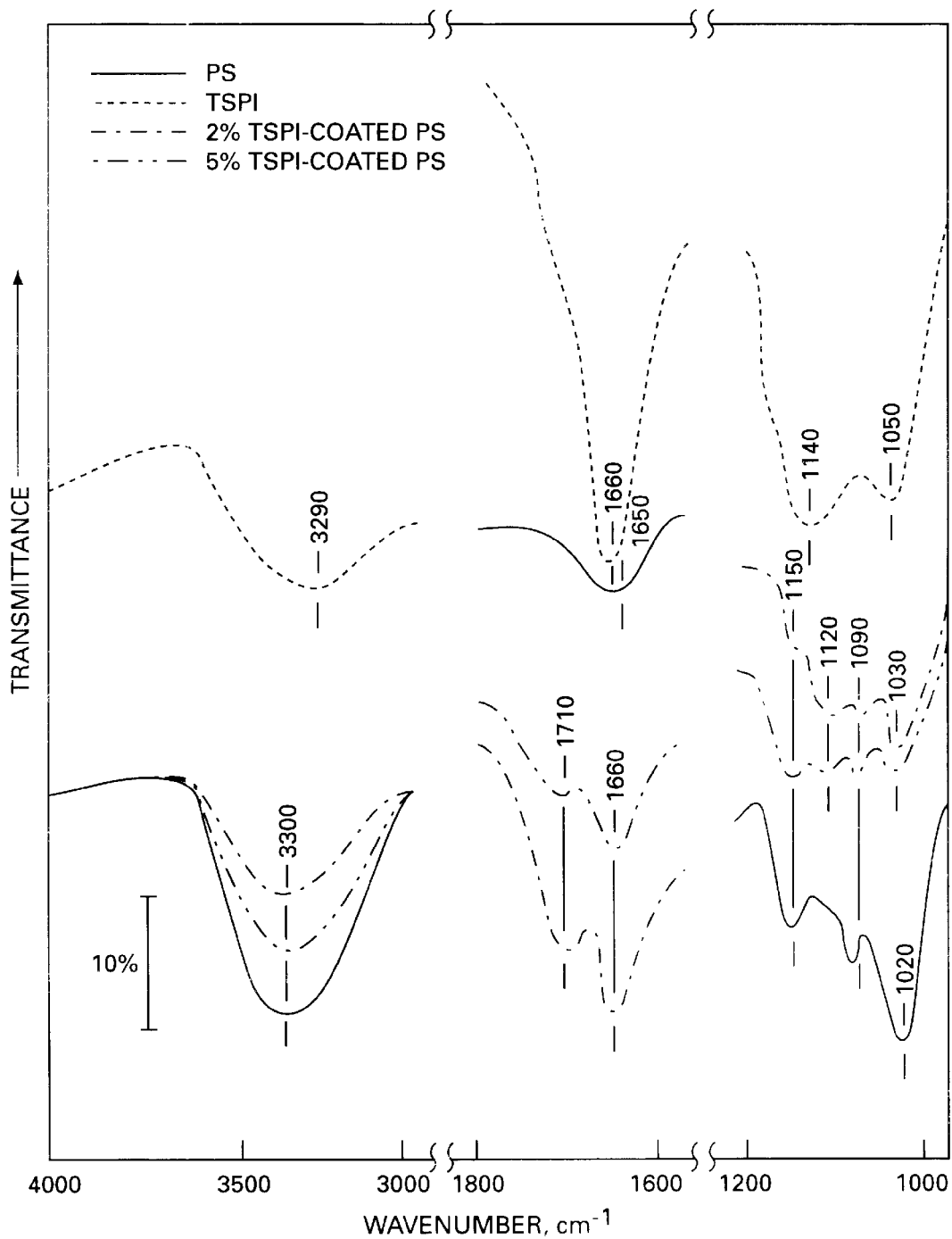
FIG. 1 shows SRFT-IR spectra for bulk PS and TSPI coating films, and 2% and 5% TSPI-coated PS films.

The present invention provides a new family of polysaccharide graft polymers, methods to make and use as corrosion-protective coatings for lightweight metal substrates. More specifically, the present invention provides natural polymers such as starch and cellulosics which have been modified with antimicrobial agents to form water impermeable corrosion resistant coating films which have antimicrobial properties.

All compounds utilized to prepare the new family of polymers of the present invention can be synthesized or are commercially available. For example, useful commercial starches include corn, wheat, rice, tapioca, potatoes and sago. Cellulosics include cellulose and its derivatives, typically esthers or ethers, cellulose xanthate, methylcellulose, hydroxyethylcellulose and carboxymethyl-cellulose.

Starch is a mixture of amylose and amylopectin. Amylose is a linear homopolysaccharide which is made up of several hundred glucose units linked by (1→4)-alpha-D-glycosidic linkages. Amylopectin is a branched homopolysaccharide of glucose units with (1→6)-alpha-D-glycosidic linkages at the branching points and (1→4)-alpha-D-glycosidic linkages in the linear region. The hydrated linear amylose molecules inherently tend to align. Once the aligned configuration is formed, intramolecular hydrogen bonds generated between the linear chains lead to an agglomeration and crystallization of amylose chains, thereby resulting in a low solubility in water. Similarly, the molecular arrangement of linear portions in branched amylopectin introduces the same degree of crystallinity into hydrated starch. However, the solubility of amylopectin in water is much higher than that of amylose. Typical starches have a proportion of 20% to 30% amylose and 70% to 80% amylopectin.

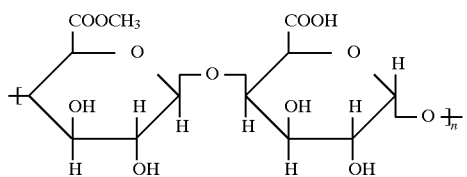

Pectin (PE) is a natural polymer also known as polygalacturonic acid methyl esther. PE has the formula shown above, wherein n is greater or equal to 500 and has a molecular weight of 20,000 to 30,000. Pectin was obtained from Scientific Polymer Products, Inc.

In order to modify the natural polymers used in the present invention, antimicrobial agents were used. For example, monomeric N-[3-(triethoxysilyl) propyl]-4,5,-dihydroimidazole (TSPI) was obtained from Huls America, Inc. or Petrarch Systems Ltd. Other useful antimicrobial agents include β-trimethoxysilyl ethyl-2-pyridine, β-trimethoxysilyl ethyl-4-pyridine, 2-[2-trichlorosilyl (ethyl]pyridine, 4-[2-(trichlorosilyl) ethyl]pyridine. Other useful antimicrobial agents include halogen-substituted silanes, such as, for example: 3-bromopropyltrimethoxysilane; 3-iodopropyltrimethoxysilane; (3,3,3-trifluoropropyl) trimethoxysilane; (3,3,3-trifluoropropyl) triethoxysilane; tridecafluoro-1,1,2,2-tetrahydrooctyl-1-triethoxysilane.

U.S. Pat. No. 4,540,777 to Amort, et al., discloses a method for the modification of starch with organofunctional alcoxysilanes and/or alkyl alcoxysilanes, in an aqueous medium. The modification of starch is performed by bringing the starch into intimate contact with hydrolyzates of the silanes in the presence of alkyl aluminates or alkyl hydroxides.

The organosilanes which could be used as modifying agents in '777 reference to Amort, et al. have the following general formula:

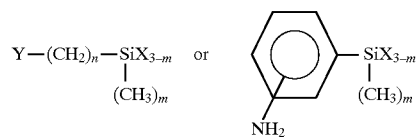

in which y represents substituted or unsubstituted amino group, or a moiety from the group H, $CH_3$, —Cl, CH=$CH_2$, —SH; X is an alcoxy moiety with a maximum of six carbon atoms; M can be 0, 1 or 2, and n takes values of 1, 2 or 3. An example of organofinctional silane includes gamma-chloropropyltrimethoxysilane. The starch disclosed in '777 reference to Amort, et al. can be used for hydrophobation and oleophobation of cellulosic material and is suitable as binder for mineral fibers, textile adjuvants, sizes for various paper products, and as fillers for plastics. The method disclosed in the '777 reference requires the presence of alkali aluminates and alkali hydroxides. Additionally, starch modified by gamma-chloropropyl trimethoxysilane does not provide the corrosion protection which is provided by bromine, iodine and fluorine substituted silanes. Moreover, the graft polymers of the present invention are prepared in the absence of alkali aluminates and alkali hydroxides.

The water-based coating systems of the present invention have been prepared by mixing solutions in two phases. One phase consisted of natural polymers dissolved in water and the other phase of a salt solution which contains an antimicrobial agent such as TSPI, water, methanol and hydrochloric acid. The resulting TSPI modified natural polymer coating films were capable of protecting lightweight metals against corrosion. Metals which can be protected with the coating films of the present invention include aluminum, magnesium, zinc, steel and alloys thereof.

Simple dip, spray or spin-coating methods can be used to deposit precursor solution layers onto the metal substrates. Heating the coated metal at temperatures from about 50° C. to about 250° C. for about 120 minutes allowed the formation of corrosion resistant coating films of the present invention.

EXAMPLES

The examples below further illustrate the various features of the invention, and are not intended in any way to limit the scope of the invention which is defined in the appended claims.

EXAMPLE 1

In this experiment, polyorganosiloxane (POS)-grafted polysaccharide copolymers were synthesized through a heat-catalyzed dehydrating condensation reaction between hydrolysates of potato starch (PS) as source of polysaccharide and N-[3-(triethoxysily)propyl]- 4,5, -dihydroimidazole (TSPI) as the antimicrobial agent and a source of the graft-forming POS at 200° C. in air. The grafting of POS onto PS followed by the opening of glycosidic rings significantly improved the thermal and hydrophobic characteristics of PS.

The experiment was also directed to evaluating the ability of antimicrobial TSPI-modified starch films to protect aluminum alloys from corrosion. The evaluations were carried out by AC electrochemical impedance spectroscopy and salt-spray resistance. The resulting data were then correlated with several other physico-chemical factors, such as the spreadability of the modified starch aqueous solution on surfaces of aluminum substrates. The magnitude of susceptibility of solid coating film surfaces to moisture, the molecular conformation of the modified starch, its thermal decomposition, and the surface morphology of films were also studied. In addition, the effect of TSPI as antimicrobial agent on preventing the settlement and growth of microorganisms in starch aqueous solution was also investigated.

1. Materials

The starch used was potato starch (PS) from ICN Biomedical, Inc. For modifying PS, monomeric N-[3-(triethoxysily)propyl]-4,5, -dihydroimidazole (TSPI) was used as supplied by Huls America, Inc. A 1.0 wt % PS solution dissolved in deionized water at 80° C. was modified by incorporating various amounts of the TSPI solution consisting of 9.5 wt % TSPI, 3.8 wt % $CH_3OH$, 1.0 wt %

HCl, and 85.7 wt % water. Six ratios of PS/TSPI solutions of 100/0, 99/1, 97/3, 95/5, 90/10, and 85/15 by weight were utilized. The lightweight metal substrate was a 6061-T6 aluminum (Al) sheet containing the following chemical constituents: 96.3 wt % Al, 0.6 wt % Si, 0.7 wt % Fe, 0.3 wt % Cu, 0.2 wt % Mn, 1.0 wt % Mg, 0.2 wt % Cr, 0.3 wt % Zn, 0.2 wt % Ti, and 0.2 wt % other elements.

2. Coating Technology

The aluminum surfaces were coated by TSPI-modified and unmodified PS films in the following sequence. The aluminum substrates were immersed for 20 minutes at 80° C. in an alkaline solution consisting of 0.4 wt % NaOH, 2.8 wt % tetrasodium pyrophosphate, 2.8 wt % sodium bicarbonate, and 94.0 wt % water in order to remove surface contaminants. The alkali-cleaned aluminum surfaces were washed with deionized water at 25° C. for 5 min, and dried for 15 min at 100° C. Then, the substrates were dipped into a soaking bath of solution at room temperature, and withdrawn slowly. The wetted substrates were then heated in an oven for 120 min at 200° to yield thin solid films.

3. Measurements

PS solutions are suitable nutrients for fungal and bacterial growth. Adding TSPI has had the effect of preventing the growth and colonization of microorganisms. This observation was verified by using scanning electron microscopy (SEM). The surface tension of the unmodified and TSPI-modified PS solutions was measured with a Cenco-DuNouy Tensiometer Model 70535. Solutions with an extremely high or low pH have been found improper for use as coatings of metal surfaces because of the corrosion of metal by such solutions. Thus, it was very important to measure the pH of coating solutions, prior to depositing them on the surface of a metal.

To understand the molecular structure of TSPI-modified PS, the films deposited on aluminum surfaces were investigated by specular reflectance fourier transform infrared (SRFT-IR) spectrophotometer, and x-ray photoelectron spectroscopy (XPS). The combined techniques of differential scanning calorimetry (DSC), thermogravimetric analysis (TGA), and differential thermal analysis (DTA) were used to assess the changes in the melting point of PS as a function of TSPI concentrations, and also to search the thermal decomposition characteristics of modified and unmodified PS polymers. The degree of crystallinity of the polymers was estimated by using x-ray powder diffraction (XRD). The changes in the magnitude of wettability and spreadability of PS solutions modified with various amounts of TSPI on aluminum surfaces were recorded by measuring the contact angle within the first 30 seconds after dropping the solution on their surfaces. The same technique was employed to obtain the water-wettability of polymer film surfaces which provided information on the degree of susceptibility to moisture of modified and unmodified PS film surfaces. Information on the surface morphology and chemical composition of films deposited to aluminum substrates was obtained by SEM and energy-dispersive x-ray (EDX) analysis.

AC electrochemical impedance spectroscopy (EIS) was used to evaluate the ability of coating films to protect aluminum from corrosion. The specimens were mounted in a holder, and then inserted into an electrochemical cell. Computer programs were prepared to calculate theoretical impedance spectra and to analyze the experimental data. Specimens with a surface area of 13 $cm^2$ were exposed to an aerated 0.5N NaCl electrolyte at 25 °C., and single-sine technology with an input AC voltage of 10 mV (rms) was used over a frequency range of 10 KHz to $10^{-2}$ Hz. To estimate the protective performance of coatings, the pore resistance, $R_{po}$, was determined from the plateau in Bode-plot scans (impedance, ohm-$cm^2$ vs. frequency, Hz) that occurred at low frequency regions. The salt-spray tests of the unmodified and modified PS-coated Al panels (75 mm×75 mm, size) were performed in accordance with ASTM B 117, using a 5% NaCl solution at 35° C.

4. Properties of Coating Films a. Growth of Microorganisms

PS polymers contain C, H, and O, among other elements which are suitable nutrients for fungal and bacterial growth. When PS comes into contact with water, inevitably the growth of microorganisms already present in the water is stimulated. As a result, bacterial colonies flourish. A serious problem in using such colonized polymer solutions as coating materials is caused by microbial bioparticles incorporated into layers of dried coating film which promote the rate of water transportation. The coating films become wet and fail as corrosion-protective coatings. Thus, adding an antimicrobial agent to a PS solution is needed to prevent the growth of microorganisms.

In the present invention, monomeric TSPI was employed as an antimicrobial agent. To assess its effectiveness on inhibiting microbial growth, 20 grams aqueous solutions having PS/TSPI ratios of 100/0 and 97/3 were placed in culture flasks, and then left for two months at 25° C. in atmospheric environments. Subsequently, these solutions were deposited on aluminum substrate surfaces by dip-withdrawal coating methods, and then dried for 24 hours in a vacuum oven at 40° C. to form solid films for SEM observations. The SEM image obtained from the unmodified PS coating disclosed a continuous coverage of extensive fungal clusters over the aluminum substrate. A strikingly different feature was observed when PS was modified with a 3 wt % TSPI solution. There was no fungal growth in the films having a 97/3 PS/TSPI ratio. This finding indicated that the incorporation of TSPI as an antimicrobial agent prevented the growth of microorganisms in PS solutions.

b. Surface Tension as a Function of pH

TABLE 1

Changes in Surface Tension and pH of PS Solutions Modified with TSPI Solutions

| PS/TSPI ratio | Surface tension dynes/cm | pH |
| --- | --- | --- |
| 100/0 | 72.3 | 6.4 |
| 99/1 | 62.4 | 8.5 |
| 97/3 | 58.9 | 8.7 |
| 95/5 | 55.4 | 8.9 |
| 90/10 | 54.8 | 8.9 |
| 85/15 | 54.7 | 8.9 |

Table 1 above shows the changes in surface tension of solutions as a function of PS/TSPI ratio at 25° C., and also their pH value. The addition of TSPI solution to PS solution decreased the surface tension, from 72.3 dynes/cm for an unmodified PS solution, to 54.7 dynes/cm for a 15 wt % TSPI-modified PS. The pH of the unmodified PS solution was 6.4; however, when this solution was modified with a 1 wt % TSPI solution, its pH shifted to a weak base value. The pH values of all TSPI-modified PS solutions ranged from 8.5 to 8.9.

c. Molecular Conformation of Modified Starch

To gain information on the interfacial reaction mechanisms between PS and TSPI, and the chemical conformation of reaction products, samples of TSPI treated PS were investigated by SRFT-IR. First, a PS solution was deposited on aluminum surfaces by dip-withdrawal coating methods, and then left for 1 hour in an oven at 100° C. to transform into a solid film. Then, the PS-coated aluminum substrates were dipped into a 2 or 5 wt % TSPI solution, and the TSPI-wetted PS coatings were treated for 2 hours with heating at 200° C. for SRFT-IR explorations.

FIG. 1 depicts the IR spectra for the 2 and 5 wt % TSPI-coated PS samples, over three frequency ranges of 4000 to 3000, 1800 to 1570, and 1220 to 970 cm$^{-1}$. For comparison, the spectra of 200° C.-heated bulk PS and TSPI coating films as the reference samples were also illustrated in this figure. A typical spectrum of the bulk PS reference coating showed absorption bands at 3380 cm$^{-1}$, revealing the OH groups in the glucose units, at 1650 cm$^{-1}$ which were ascribed to the bending vibration of H—O—H in the adsorbed H$_2$O, and also at 1150, 1090, and 1020 cm$^{-1}$, reflecting the stretching mode of C—O—C linkages in the glycosidic rings. The spectrum of bulk TSPI film showed an OH stretching band of adsorbed H$_2$O at 3290 cm$^{-1}$, a —C=N— band of dihydroimidazole coexisting with the H—O—H bending in H$_2$O at 1660 cm$^{-1}$, a Si—O—C bond of the Si-joined alkoxy groups at 1140 cm$^{-1}$, and Si—O—Si linkages at 1050 cm$^{-1}$.

When PS was coated with 2 wt % TSPI, the particular features of the IR spectrum differed from those of the reference samples. There was a decrease in intensity of the absorption band at 3380 cm$^{-1}$, (ii) a development of three new bands at 1710, 1120, and 1030 cm$^{-1}$, and (iii) a striking reduction of intensity of the C—O—C linkage-related bands in the frequency regions of 1200 to 1000 cm$^{-1}$. Increasing the concentration of TSPI to a 5 wt % led to a further decrease in intensity of the OH and C—O—C bands, while a marked growth of these new bands could be seen in the spectrum. The contributor to the new band at 1710 cm$^{-1}$ is likely to be the C=O groups. On the other hand, the Si-alkoxy compounds and siloxanes have strong bands in the ranges of 1170–1110 cm$^{-1}$ and 1110–1000 cm$^{-1}$, respectively. Thus, without being bound by theory, it has been concluded that the new bands at 1120 and 1030 cm$^{-1}$ showed the formation of Si—O—C and Si—O—Si linkages, respectively. If this interpretation is correct, Si—O—C not only belongs to that linkage in the TSPI, but also may be due to the reaction products formed by the interaction between PS and TSPI. The Si—O—Si linkage is the embodiment of forming the polysiloxane structures.

In the study of the mechanism of graft copolymerization onto polysaccharide initiated by metal ion oxidation reaction, Doba et al., in Macromolecules, 17, p. 2512, 1984 have shown that oxidation of glycol groups in the glycosidic rings by ionic metal species cleaved the glycol C—C bond. The opening of the rings caused by such a cleavage not only generated a free radical which promoted the grafting of the vinyl monomers onto the polysaccharides, but also provided the formation of C=O groups. Also, they reported that no free radicals were found at the C position of —CH$_2$OH groups in the glucose units. Relating this finding to the fact that the spectrum of the bulk PS film does not show a clear feature of C=O bands, the development of C=O groups in the TSPI-coated PS is thought to involve the formation of Si—O—C linkages yielded by a dehydrating condensation reaction between the one hydroxyl, OH of glycol groups and the silanol group Si—OH in the hydrolysate of TSPI, followed by opening of ring. However, there was no evidence as to whether a free radical had been generated. Moreover, such a condensation reaction may also occur between the OH of —CH$_2$OH group in the glucose units and the OH of silanol group to form the Si—O—C linkages.

Because the polysiloxane structure is present in the reaction products, the creation of these linkages virtually demonstrated that the polyorganosiloxanes (POS) were grafted to the PS.

Figure 2A:
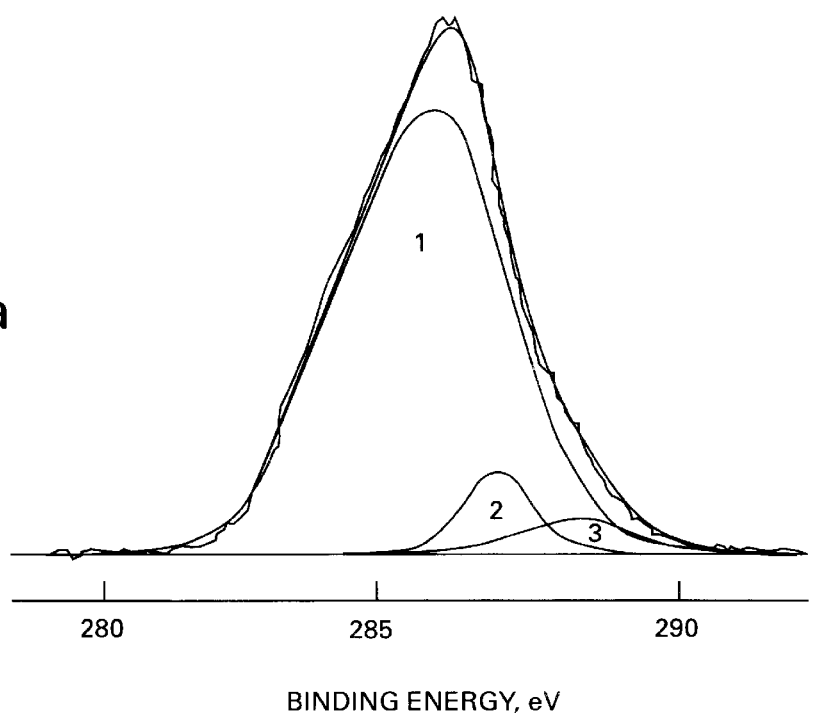
FIGS. 2(a) and 2(b) show XPS $C_{1s}$ core-level spectra at (a) for bulk PS and at (b) for TSPI-modified PS coating surfaces at 200° C.; the peak positions for each curves 1, 2, and 3 correspond to 285.0, 286.5, and 288.0 eV, respectively.
Figure 2B:
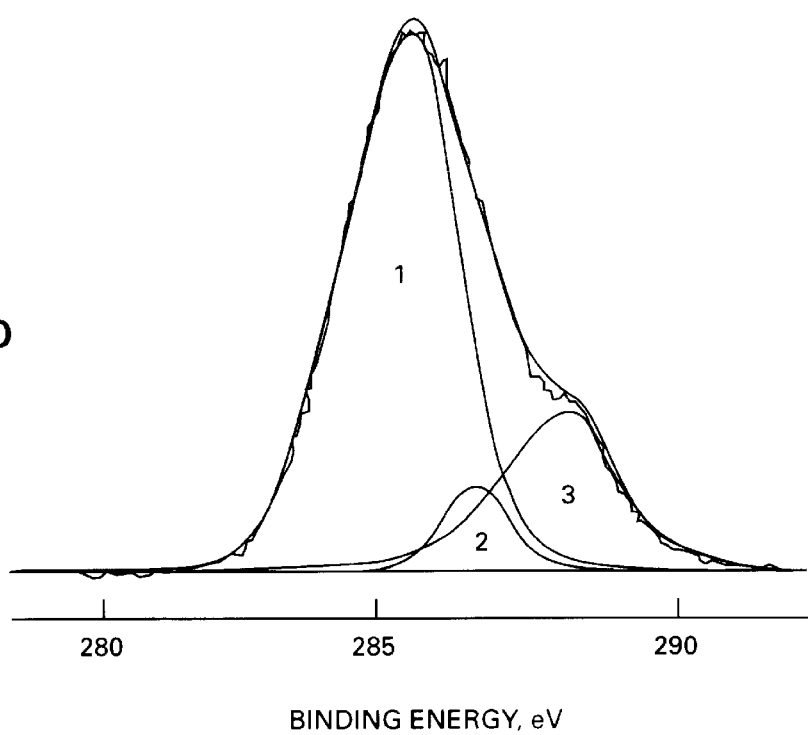

To further ascertain that C=O groups were generated, the XPS $C_{1s}$ core-level excitations for the 200° C.-heated film surfaces with PS/TSPI ratios of 100/0 and 85/15 were inspected. In this core-level spectra, the scale of the binding energy (BE) was calibrated with the $C_{1s}$ of the principal hydrocarbon-type carbon peak fixed at 285.0 eV as an internal reference standard. A curve deconvolution technique, using a Du Du Pont curve resolver, was employed to support the information on the carbon-related chemical states from the spectrum of the carbon atom. As shown in FIG. 2, the $C_{1s}$ region of bulk PS surfaces had three resolvable Gaussian components at the binding energy (BE) positions of 285.0, 286.5, and 288.0 eV denoted as peak areas "1", "2", and "3". The major peak at 285.0 eV is associated with the C in CH$_2$ and CH groups as the principal component. According to established literature sources, the second most intensive peak at 286.5 eV is attributable to the C in —CH$_2$O— (e.g. alcohol and ether), while a very weak signal, emerging at 288.0 eV, originates from C in the C=O groups. Although the thermal treatment of PS film at 200° C. in air may introduce C=O into the PS surfaces as the oxidation product, it was assumed from the curve feature that the number is very low. In contrast, the curve structure of TSPI-modified PS film is quite different from that of bulk PS film. In particular, there is a significant growth of the C=O peak and there is a marked decay of C—O signal intensity. These findings strongly supported the results obtained from the IR study, namely, the grafting of POS onto PS promotes the development of C=O groups within the PS structure, thereby causing the opening of the glucose ring.

From this information, the graft structures set forth below is proposed. It is not clear whether the opening of the ring leads to the formation of a free radical or a saturated group.

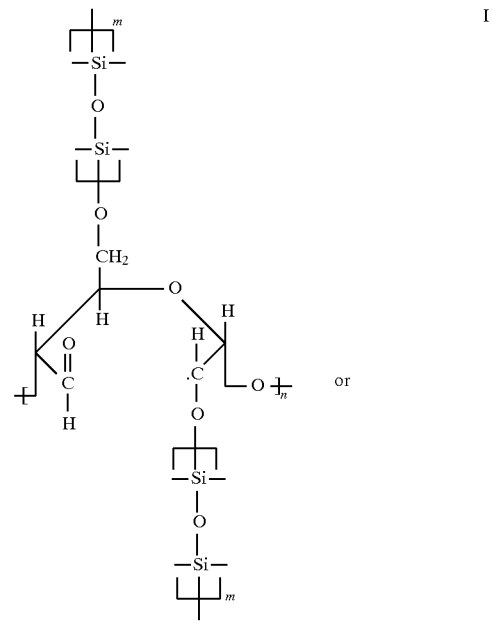

-continued

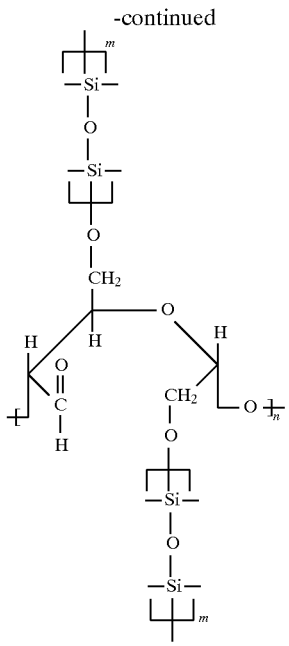

II d. Thermal Characteristics

Figure 3:
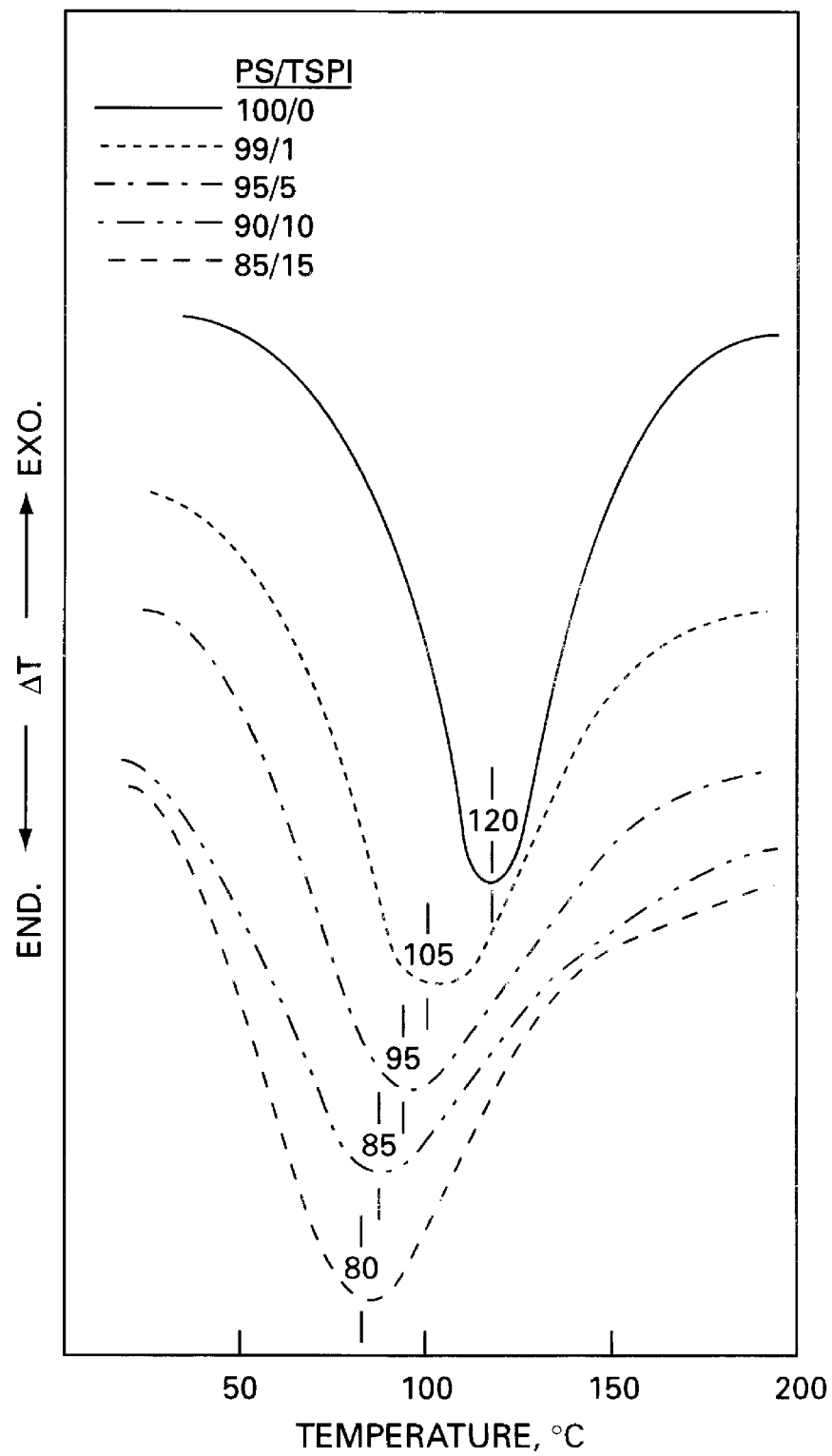
FIGS. 3 illustrates a shift in the endothermal temperature of PS to low values when the proportion of TSPI to PS was increased.

Thermal characteristics, such as melting point, thermal degradation, and stability, of 200° C.-heated samples with PS/TSPI ratios of 100/0, 99/1, 95/5, 90/10, and 85/15 have been studied. FIG. 3 illustrates the DSC endothermic phase transitions occurring in these samples at temperatures ranging from 25° C. to 170° C. As reported by Lelievre in J. Appl. Poly. Sci., 18, p. 293, 1973 and Donovan in Biopolymers, 18, p. 263, 1979, the temperature of the endothermal peak for hydrated starches depended primarily on the degree of its hydration; namely, the starch with a low degree of hydration had the endothermal peak at higher temperature. They interpreted that a shift in the endothermal peak to a high temperature site corresponds to an increase in melting point of starch. From this information, the endothermal peak at 120° C. for bulk PS (100/0 ratio) was similar to that obtained from their samples containing a minimum amount of water.

When PS was modified with TSPI, the endothermic temperature expressed as the melting point ($T_m$) decreases with an increasing amount of TSPI, suggesting that the $T_m$ shifts to low temperature site as the number of POS grafts per PS chain unit is increased. In other words, the cleavage of glycol C—C bonds which occurred when POS was grafted onto glycosidic rings might cause a lowering of $T_m$, reflecting a low rate of PS hydration. The enthalpy, $\Delta H$, of this phase transition was computed using the formula $\Delta H = T \cdot R \cdot A / h \cdot m$, where T, R, A, h, and m refer to temperature scale (° C./in.), range sensitivity (mcal./sec.-in.), peak area (in$^2$), heating rate (° C./sec), and weight of the sample (mg), respectively. The changes in $\Delta H$ as a function of the proportion of PS to TSPI are given in Table 2 below.

TABLE 2

Changes in Enthalpy which Represent the Rate of PS Hydration as a Function of PS/TSPI Ratios

| PS/TSPI ratio | Enthalpy value, $\Delta H$ KJ/g |
|---|---|
| 100/0 | 0.325 |
| 99/1 | 0.266 |
| 97/3 | 0.240 |

TABLE 2-continued

Changes in Enthalpy which Represent the Rate of PS Hydration as a Function of PS/TSPI Ratios

| PS/TSPI ratio | Enthalpy value, $\Delta H$ KJ/g |
|---|---|
| 95/5 | 0.176 |
| 90/10 | 0.136 |
| 85/15 | 0.119 |

From Table 2 above, it is apparent that the value of $\Delta H$ decreases with an increasing amount of TSPI incorporated into PS. Because the $\Delta H$ value reflects the total energy consumed for breaking the intermolecular hydrogen bonds generated between starch and water, it was assumed that a high degree of POS grafts might lead to a molecular configuration of PS chains with fewer hydrogen bonds.

Figure 4:
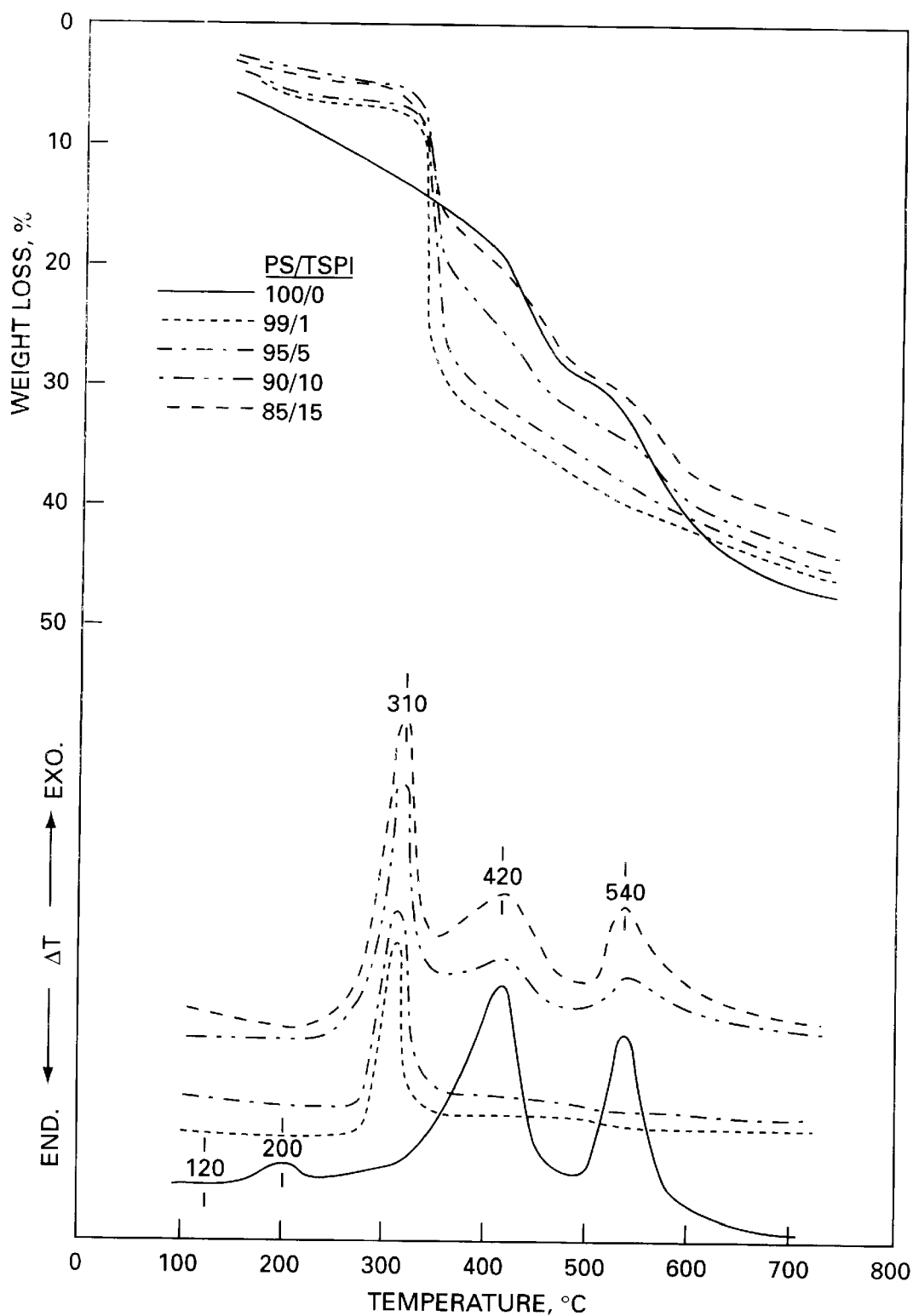
FIG. 4 shows TGA and DTA curves for 200° C.-heated bulk PS and TSPI-modified PS polymers.

A thermal analysis, combining TGA and DTA, revealed the decomposition characteristics during pyrolysis of 200° C.-heated samples as shown in FIG. 4. The TGA curve (top) for the bulk PS, showed a certain rate of loss in weight between 30° C. and 150° C., followed by large reductions in the two temperature ranges, 300° C.–400° C. and 450° C.–600° C., and then a small decrease between 600° C. and 700° C. The loss in weight occurring at each individual stage in the four-step decomposition process gave the following values: about 10% at temperatures up to 200° C., about 19% between 200° C. and 450° C., about 16% between 450° C. and 600° C., and about 3% between 600° C. and 700° C. By comparison with the TGA curve of bulk PS, the changes in the feature of the curve were seen in samples in which TSPI was incorporated. The addition of TSPI to PS greatly reduced the weight loss in the first decomposition stage. Considering that the weight loss at temperatures up to 200° C. was due mainly to dehydration of the samples, it is believed that the samples heated to 200° C. and which had a high proportion of TSPI to PS had a lesser uptake of moisture. For all the TSPI-modified PS samples, the onset temperature of the second decomposition stage was near 280° C. Of particular interest were also the features of curves obtained for samples 99/1 and 95/5 PS/TSPI ratio. These curves were different from those obtained for samples having 90/10 and 85/15 having PS/TSPI ratios; namely, the latter samples had two additional decomposition stages at temperatures ranging from 310° C. to 600° C.; by contrast, the 99/1 and 95/5 ratio PS/TSPI samples were characterized by a large decrease between 280° C. and 340° C., followed by a gradual loss in weight after 340° C. In these additional stages, one of the decompositions occurred between 310° C. and 470° C., and the other was in the ranges from 470° C. to 600° C. These additional decomposition stages have been assigned to POS polymers. Thus, a high proportion of TSPI to PS appeared to provide an individual POS formation segregated from the POS-grafted PS polymer systems. If this interpretation is correct, the decomposition occurring between 280° C. and 340° C. could correspond to the formation of POS-grafted PS polymers as the reaction products. In fact, no such decomposition was found from bulk PS samples.

Significantly, the DTA curves (bottom) accompanying the TGA data strongly supported the information described above. The curve of bulk PS indicated the presence of three prominent endothermic peaks at 95° C., 410° C., and 500° C. Because a DTA endothermic peak represents the phase transition temperature caused by the thermal decomposition of chemical compounds, the peak at 95° C. reveals the dehydration of PS, while the removal of carbonaceous groups from the PS structure may be associated with the peaks at 410° and 500° C. In contrast, the 99/1 and 95/5 ratio of PS/TSPI samples had only two endothermic peaks at 95° C. and 310° C. The former peak appeared to be due to the elimination of water from the TSPI-modified PS polymers, and the latter could reveal the decomposition of POS-grafted PS polymers. No peaks at 410° C. and 500° C. were recorded on the DTA curves. As expected, the peak intensity at 95° C. decreased with an increasing amount of TSPI, suggesting that a highly grafted POS onto PS lead to a low rate of hydration of PS. Assuming that the peak at 310° C. was related to the grafted PS polymers, the growth of its line intensity resulting from the incorporation of a large amount of TSPI into PS indicated that the extent of POS grafting was promoted by an increased amount of TSPI. The peaks at 400° C. and 540° C. for the 90/10 and 85/15 ratio samples were assignable to the phase transition temperatures of POS itself isolated from the grafted PS. The intensity of these peaks increased with an increase in the proportion of TSPI to PS, implying that the extent of non-grafted bulk POS existing in the whole polymer structure increased as an excessive amount of TSPI was added to PS.

It is well documented that the hydration of starch introduces crystallinity into the amylose portion and linear branching of amylopectin. Thus, the degree of crystallinity of unmodified and TSPI-modified PS samples were investigated after heating at 200° C., by XRD. The resulting XRD patterns, ranging from 0.256 to 0.590 nm, (not shown) revealed that all the samples were essentially amorphous. Because the formation of an amorphous phase was due mainly to the low rate of hydration of starch, it was assumed that the two major factors, the treatment at 200° C. and the opening of glycosidic rings by grafting of POS onto the PS, may cause a poor hydration of starch.

5. Characteristics of Coated Surfaces

Based upon the information described above, the characteristics of the TSPI-modified PS coating films deposited onto surfaces of aluminum substrate were analyzed next. The characteristics to be investigated involved the magnitude of wettability and spreadability of PS solutions modified with TSPI onto aluminum surfaces, the morphological features and elemental compositions of the coating films, and the susceptibility of the film surfaces to moisture. All of the data obtained were correlated directly with the results from the corrosion-related tests, such as electrochemical impedance spectroscopy (EIS) and salt-spray resistance tests.

a. Wettability of Coated Surfaces

Figure 5:
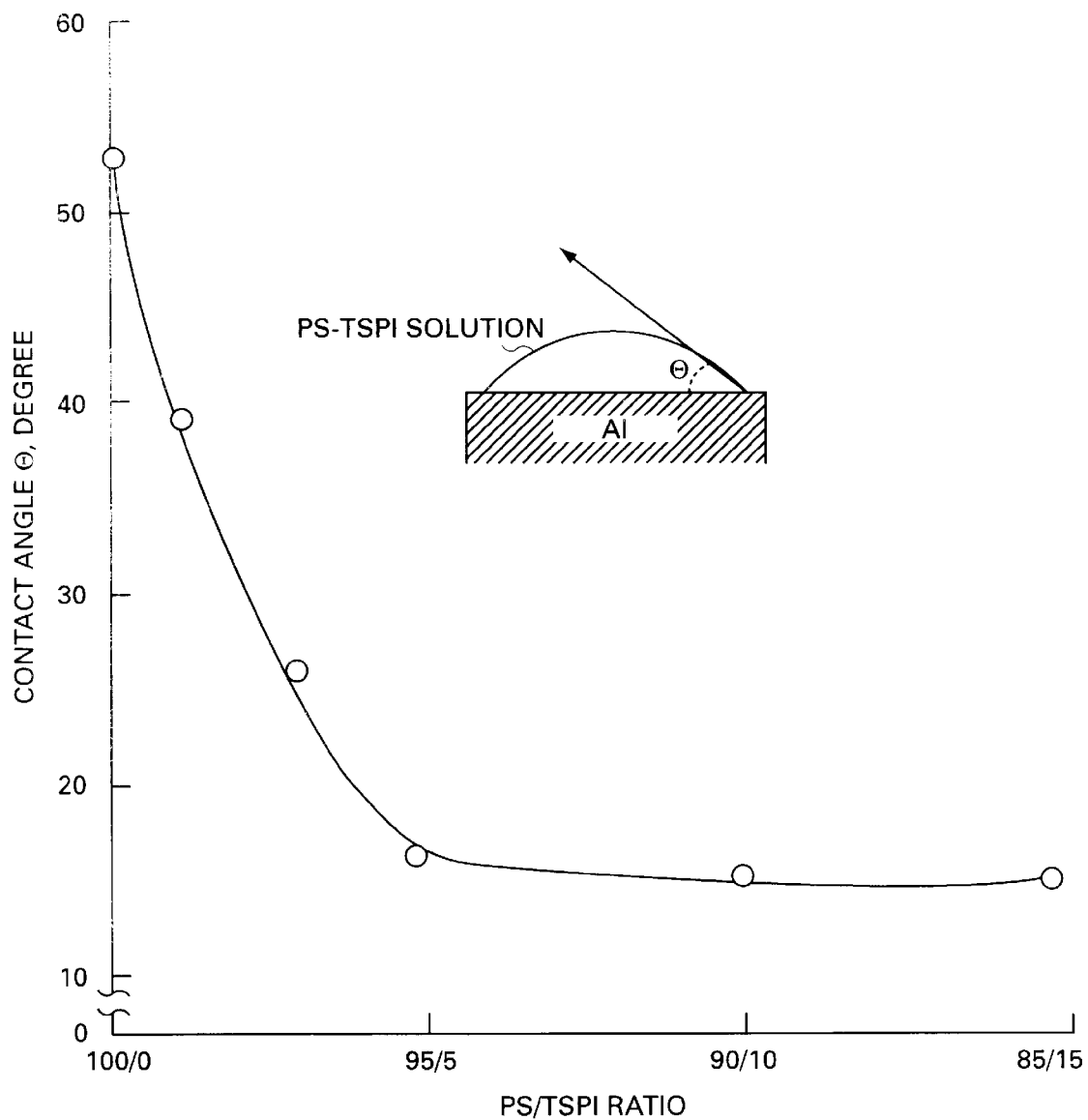
FIG. 5 illustrates contact angles of various different PS/TSPI ratio solutions which were dropped on surfaces of aluminum substrates.

In forming uniform, continuous coating films, the magnitude of wettability and spreadability of the alkali-cleaned aluminum surfaces by TSPI-modified PS solutions was among the most important factors governing good protective-coating performance. In an earlier study on the chemical composition of aluminum surfaces treated with a hot alkali solution, I have reported that such surface preparation method introduces an oxide layer into the outermost surface sites of aluminum. See Sugama, T., et al., in J. Coat. Tech., 65, p. 27, 1993. Hence, the magnitude of the wettability of the unmodified and TSPI-modified PS solutions over the aluminum oxide layers was estimated from average values of the advancing contact angle, θ (in degrees), on this surface. A plot of θ as a function of the PS/TSPI ratios is shown in FIG. 5. Because a low contact angle implied better wetting, the resultant θ-ratio data exhibited an interesting feature, namely, the wetting behavior was improved by increasing the proportion of TSPI to PS. In fact, a considerable low θ value of <18°, compared with that of the 100/0 ratio, was measured from the 95/5, 90/10, and 85/15 ratio PS/TSPI solutions, suggesting that the chemical affinity of the PS solution for the aluminum oxide surfaces was significantly improved by incorporating TSPI into it.

Figure 6A:
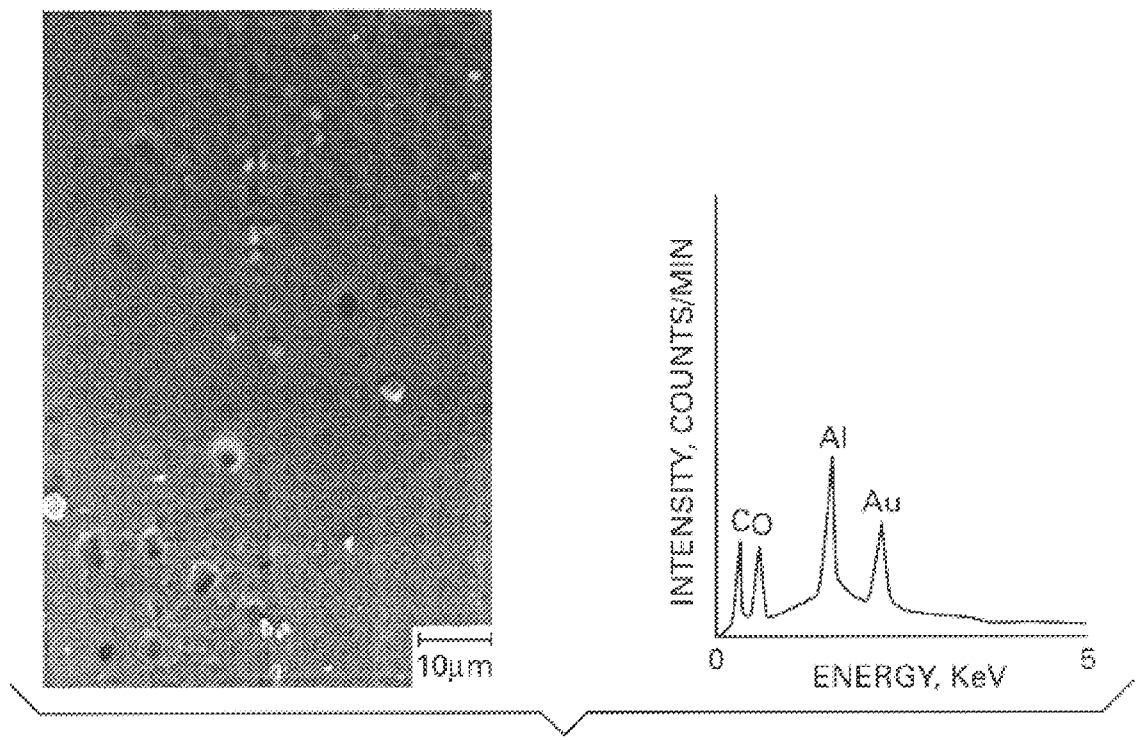
FIG. 6 shows SEM micrographs coupled with EDX spectra for 200° C.-treated film surfaces with 100/0 (top) and 95/15 (bottom) PS/TSPI ratios.
Figure 6B:
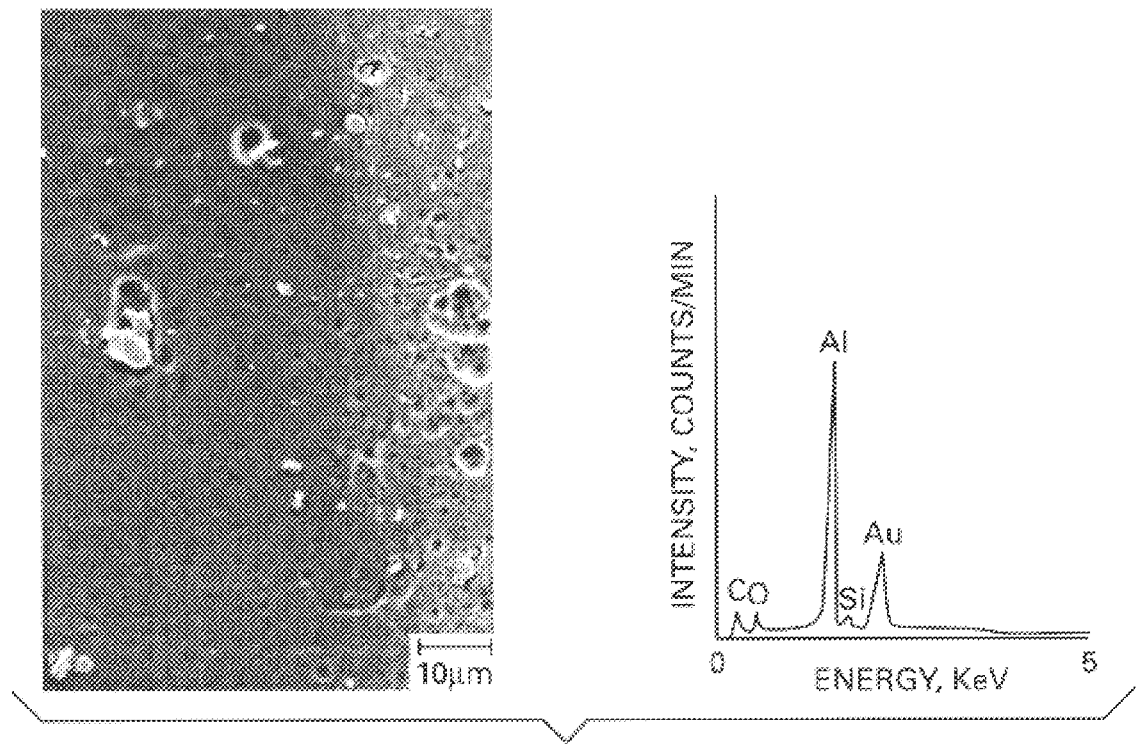

The surface image and elemental analyses for 200° C.-treated 100/0, 95/5, 90/10, and 85/15 ratio films over the aluminum substrates were carried out by SEM and EDX. The SEM image of 100/0 ratio film shown in FIG. 6 at the top) disclosed the morphological feature as a rough, thick coating film. The EDX spectrum, concomitant with the SEM micrographs, for this film, indicated the presence of four dominant lines of C, O, Al, and Au. The detected Au corresponds to that used as the sputtering material over the film surfaces. Because EDX is useful for quantitative analysis of elements which exist in the subsurface layer of up to about 1.5 μm in thickness, the aluminum element virtually belongs to the underlying substrate, while the C and O elements are assignable to the PS film. Hence, the thickness of this film is less than 1.5 μm. In contrast, the SEM image of coatings derived from the 95/5 ratio showed a continuous film covering the aluminum substrate as illlustrated at the bottom of FIG. 6. The disclosure of a rough underlying aluminum surface expressed the formation of a thin, transparent film. As expected, the EDX spectrum of this film had a dominant peak for Al, and weak C, O, and Si signals which revealed the formation of POS-grafted PS polymer films. Relating this finding to the fact that the spreadability of PS solution over the Al was significantly improved by incorporating TSPI, such a high magnitude of spreadability by TSPI-modified PS solutions perhaps provided the fabrication of thin coating film on Al. However, no determination of film thickness was made in this experiment. By comparison with that of the 95/5 ratio PS/TSPI film, no distinctive features were seen in the SEM images (not shown) from the 90/10 and 85/15 ratio PS/TSPI films. The EDX spectra for these films demonstrated that a very thin film was formed from 90/10 and 85/15 ratio solutions because of the indication of a firther intense Al signal.

b. Susceptibility of Coated Surfaces to Moisture

One important factor which is indispensable for good protective coating systems is good hydrophobic characteristics, namely the film coated surfaces are not susceptible to moisture. To obtain information on these characteristics, we measured the contact angle of a water droplet on the 200° C.-treated 100/0, 95/15, 90/10, and 85/15 ratio of PS/TSPI covered aluminum film surfaces. For instance, if the contact angle was low, we concluded that the film is susceptible to moisture. A high degree of susceptibility could allow the hydrolytic decomposition of the film and the penetration of water through the coating layers.

Figure 7:
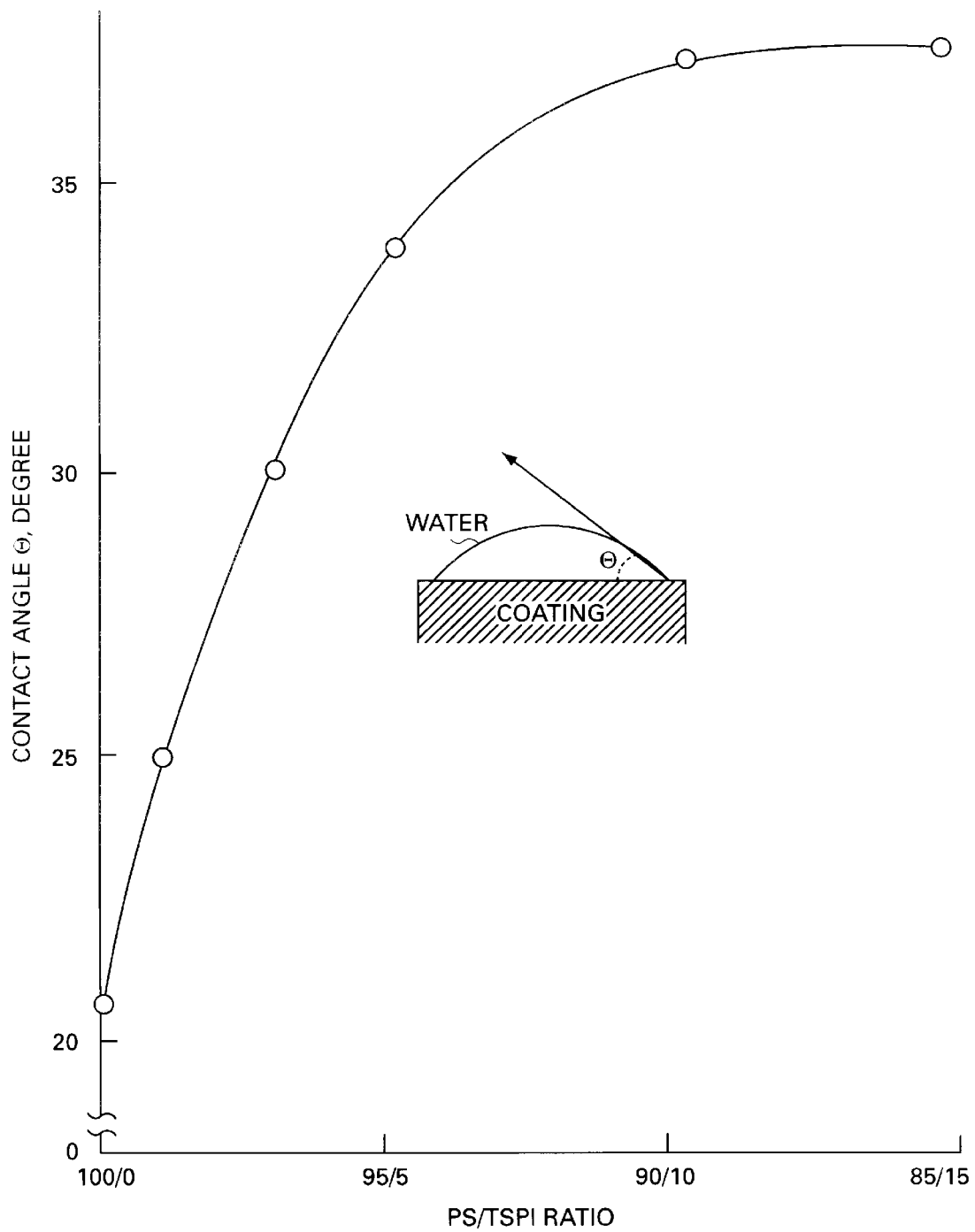
FIG. 7 illustrates contact angle of a water droplet on 200° C.-treated coating films with different PS/TSPI ratios.

A plot of the contact angles against the changes in PS/TSPI ratio is shown in FIG. 7. The data set forth in FIG. 7 shows that a decrease in this ratio enhanced the contact angle, corresponding to a low degree of wettability of the film surface. The highest value of contact angle in this test series was obtained from the 90/10 and 85/15 ratios of PS/TSPI coatings, reflecting their low susceptibility to moisture.

All these data were correlated directly with the results from the electrochemical impedance spectroscopy (EIS) for the 100/0, 95/5, 90/10, and 85/15 ratio of PS/TSPI coated aluminum specimens at 200° C. An uncoated Al substrate was also used as the reference sample.

Figure 8:
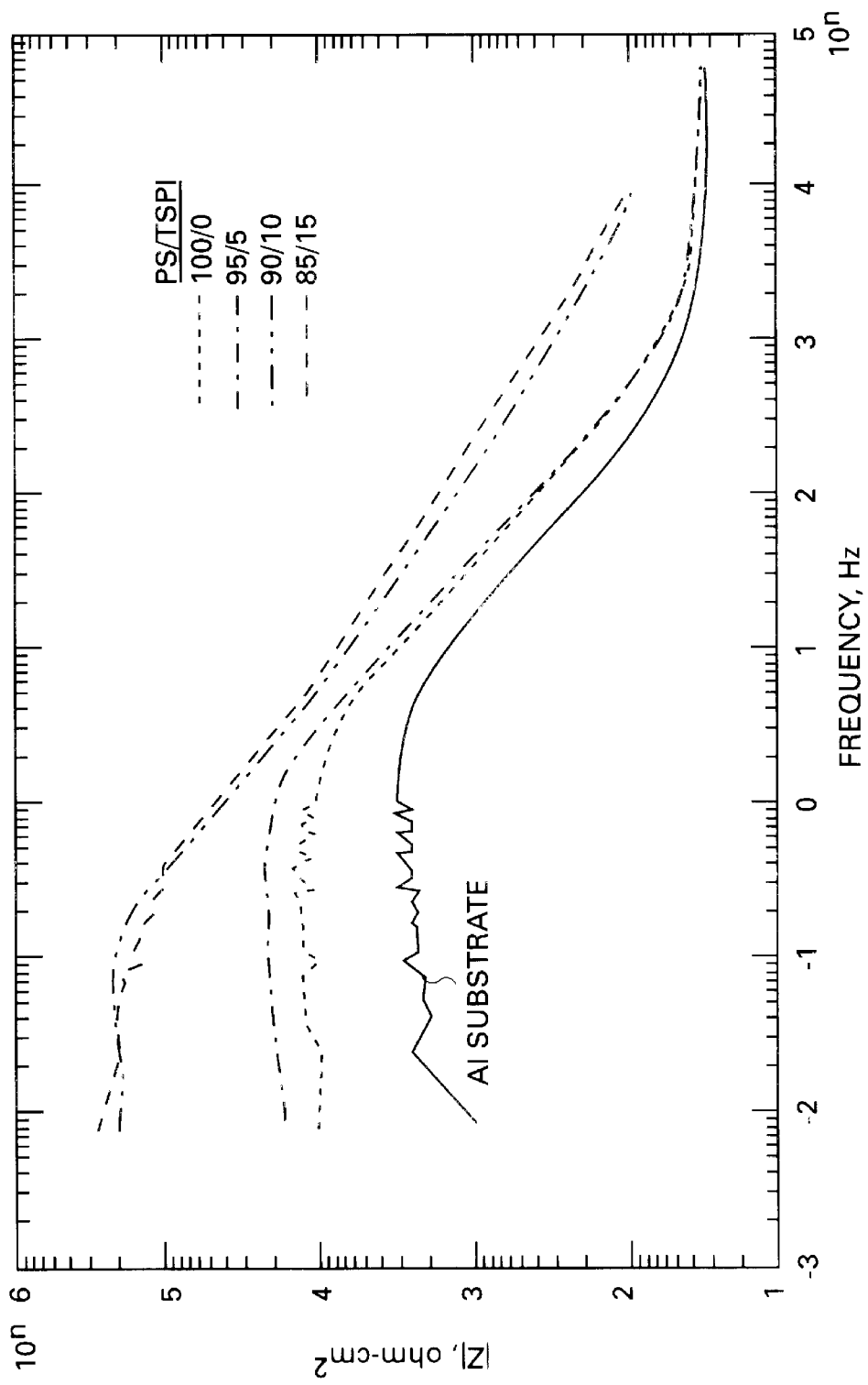
FIG. 8 shows Bode-plots for bare aluminum substrate, and aluminum specimens coated with films having 100/0, 95/5, 90/10, and 85/15 PS/TSPI ratios.

FIG. 8 compares the Bode-plot features (the absolute value of impedance, $|Z|$, ohm-cm$^2$ vs. frequency, Hz) of these specimens before exposure. As regards the overall impedance curve our tests focused on the impedance value of element $|Z|$, which can be determined from the plateau in the Bode plot occurring at sufficiently low frequencies. The impedance of the uncoated aluminum substrate was ≈3.0× 10$^3$ ohm-cm$^2$ at a frequency of 0.0 Hz. Once the aluminum surface was coated with unmodified and TSPI-modified PS films, the impedance in the terms of pore resistance, $R_{po}$, of the coatings increased by one or two orders of magnitude over that of the substrate. The $R_{po}$ values reflect the magnitude of ionic conductivity generated by the electrolyte passing through coating layers; namely, a high value of $R_{po}$ corresponds to a low degree of penetration of electrolyte into the coating film. The data demonstrated that the changes in the magnitude of conductivity depend on the PS/TSPI ratios. The data also showed that the curve feature of 90/10 ratio-derived coating closely resembled that of the 85/15 ratio PS/TSPI coating, suggesting that the ability of 90/10 ratio coating to prevent the penetration of electrolyte is almost the same as that of 85/15 ratio. From the comparison of $R_{po}$ values at $5\times10^{-2}$ Hz, the effectiveness of these ratios in ensuring a low degree of penetration of electrolyte was in the following order; 85/15=90/10>95/5>100/0. Thus, the 85/15 and 90/10 ratio-derived PS/TSPI coating films displayed a good protective performance of aluminum against corrosion.

c. Salt Spray Resistance Tests

To support the data obtained from EIS, salt-spray resistance tests were carried out for all coated specimens. The trace of rust stain was generally looked for in evaluating the results from salt-sprayed specimens.

TABLE 3

Salt-Spray Resistance Tests for TSPI-Modified PS Coatings

| PS/TSPI ratio | Salt-spray resistance Hr |
|---|---|
| 100/0 | 24 |
| 99/1 | 24 |
| 97/3 | 24 |
| 95/5 | 48 |
| 90/10 | 288 |
| 85/15 | 288 |

As shown in Table 3 above, the results were reported as the total exposure time at the date of the generation of rust stain from Al surfaces. The surfaces of the 100/0, 99/1, and 97/3 ratio coatings were corroded after exposure to salt fog for only 24 hours. By comparison with these coatings, a better protective performance for 48 hours was obtained from the 95/5 ratio-coated specimens. In contrast, the deposition of the 90/10 and 85/15 PS/TSPI ratio coatings onto aluminum contributed remarkably to protecting it from salt-induced corrosion for 288 hrs. This finding was similar to the data obtained on EIS, namnely, the most effective thin coating film for protecting aluminum alloys against corrosion can be prepared by using the solutions having ratios of 90/10 and 85/15 PS/TSPI ratios.

In conclusion, in applying the polyorganosiloxane (POS) polymers grafted onto polysaccharide as thin coating films, adequate protection from corrosion to aluminum alloys was provided. The precursor hydrolysate solutions with a pH of 8.5–8.9 were prepared by incorporating monomeric N-[-3-(triethoxysilyl)propyl]-4,5, -dihydroimidazole (TSPI) as source of graft-forming POS into a 1.0 wt % potato starch (PS) aqueous solution as source of polysaccharide. The monomeric TSPI solutions consisted of 9.5 wt % TSPI, 3.8 wt % $CH_3OH$, 1.0 wt % HCl, and 85.7 wt % water. In this system, TSPI played an important role in preventing the settlement and growth of microorganisms in PS aqueous solution. One of the important properties for TSPI precursor solution was that the surface tension of PS hydrolysate could be reduced by adding TSPI hydrolysate, thereby assuring its excellent wetting behavior on aluminum surfaces.

The high magnitude of wettability was responsible for fabricating a thin solid film over aluminum surfaces. When the precursor solution-solid phase conversion occurred at 200° C. in air, the grafting of TSPI-derived POS polymer onto PS was produced by dehydrating condensation reactions between silanol groups in the hydrolysate of TSPI, and the OH groups of glycol and $CH_2OH$ in the glucose units. Such reactions of silanol with one OH of glycol groups also led to the cleavage of glycol C—C bonds, causing the opening of glycosidic rings. Thus, an increase in the number of POS grafts shifted the melting point of PS to a low temperature site, thereby forming the molecular configuration of PS chains with few hydrogen bonds between PS and water. Although the onset of major thermal decomposition of POS-grafted PS polymers began near 280° C., the loss in weight of POS-PS copolymers occurring between 280° C. and 700° C. depended mainly on the number of POS grafts; a high degree of grafting corresponded to a low rate of weight reduction. However, the addition of an excessive amount of TSPI to PS caused the phase segregation of non-grafted POS polymers from its copolymer phases.

The most effective amorphous coating films for preventing the corrosion of aluminum surfaces were derived from precursor solutions with PS/TSPI ratios of 90/10 and 85/15. These coating films deposited onto an aluminum surface displayed a low susceptibility to moisture, improved impedance, $\Omega\text{-cm}^2$ by two orders of magnitude over that of an uncoated aluminum substrate, and conferred salt-spray resistance for 288 hours.

EXAMPLE 2

In this example, environmentally benign natural polymers in water-based coating material systems were provided to protect aluminum (Al) substrates from corrosion. Polygalacturonic acid methyl ester or pectin (PE) which belongs to a family of natural polymers was modified with N-[3-(triethoxysilyl)propyl]-4,5-dihydroimidazole (TSPI). The water-based coating systems were prepared by mixing solutions of two phases; one was PE dissolved in water, and the other was a sol solution, consisting of TSPI, water, $CH_3OH$, and HCl. In this system, TSPI played an important role in preventing the settlement and growth of microorganisms in PE aqueous solution.

1. Materials

The materials used to make the polysaccharide graft polymers and coatings including these polymers have been synthesized as set forth below or are readily commercially available.

Polygalacturonic acid methyl ester,

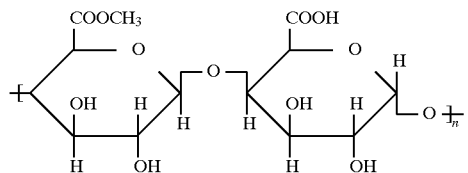

(pectin, PE), with M.W. 20,000–30,000, obtained from Scientific Polymer Products Inc., was used as the natural polymer. For modifying this polymer, monomeric N-[3-(triethoxysilyl)propyl]-4,5,-dihydroimidazole (TSPI),

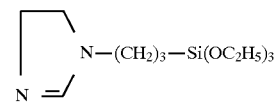

was supplied by Petrarch Systems Ltd. The estimated purity level of these organic reagents was greater than 99.8%. A 0.7 wt % PE solution dissolved in deionized water was modified by incorporating various amounts of TSPI solution consisting of 9.5 wt % TSPI, 3.8 wt % $CH_3OH$, 1.0 wt % HCl, and 85.7 wt % water. Six ratios of PE/TSPI solutions were used, namely, 100/0, 99/1, 97/3, and 95/5 by weight, corresponding to pH value of 3.40, 3.68, 6.37, and 7.55, respectively.

The lightweight metal substrate was 6061-T6 aluminum (Al) sheet, containing the following chemical constituents: 96.3 wt % Al, 0.6 wt % Si, 0.7 wt % Fe, 0.3 wt % Cu, 0.2 wt % Mn, 1.0 wt % Mg, 0.2 wt % Cr, 0.3 wt % Zn, 0.2 wt % Ti, and 0.2 wt % other.

2. Coating Method

Aluminum surfaces were coated by TSPI-modified and unmodified PE films in the following sequence. As the first step to remove surface contaminants, the aluminum substrates were immersed for 20 min at 80° C. in an alkaline solution consisting of 0.4 wt % NaOH, 2.8 wt % tetrasodium pyrophosphate, 2.8 wt % sodium bicarbonate, and 94.0 wt % water. The alkali-cleaned aluminum surfaces were washed with deionized water at 25° C. for 5 minutes, and dried for 15 minutes at 100° C. Then, the substrates were dipped into a soaking bath of solution at room temperature, and withdrawn slowly. The wetted substrates were heated in an oven for 120 min at either 50°, 80°, 100°, 150°, 200°, or 250° C. to yield thin solid films. Because the PE solution is a suitable nutrient for fungal and bacterial growth, the effect of adding TSPI was to prevent the growth and colonization of microorganisms.

3. Measurements

The antibacterial properties of the coatings of the present invention were measured by using scanning electron microscopy (SEM) and energy-dispersion X-ray (EDX). The changes in chemical conformation of PE modified with different amounts of TSPI were investigated by fourier transform infrared (FT-IR) spectrophotometer. To determine the maximum allowable temperature needed for fabricating the coating films, the onset of thermal decomposition in modified and unmodified PE polymers was measured using thermogravimetric analysis (TGA) in air. The changes in magnitudes of water-wettability of PE film surfaces with various amounts of TSPI were recorded by measuring the contact angle within the first 30 seconds after dropping water on their surfaces. The resulting data provided information on the degree of susceptibility to moisture of modified and unmodified PE film surfaces. Information on the bond structure assembled at interfaces between modified PE film and Al was obtained using X-ray photoelectron spectroscopy (XPS). These data were correlated directly with the corrosion-related information.

AC electrochemical impedance spectroscopy (EIS) was used to evaluate the ability of coating films to protect Al from corrosion. The specimens were mounted in a holder, and then inserted into an electrochemical cell. Computer programs were prepared to calculate theoretical impedance spectra and to analyze experimental data. Specimens with a surface area of 13 cm$^2$ were exposed to an aerated 0.5N NaCl electrolyte at 25° C., and single-sine technology with an input AC voltage of 10 mV (rms) was used over a frequency range of 10 KHz to 1 MHZ. The lower frequency limit was chosen because of time limitations. To estimate the protective performance of coatings, the pore resistance, $R_{po}$, was determined from the plateau in Bode-plot scans (impedance, ohm-cm$^2$ vs. frequency, Hz) that occurred at low frequency regions.

4. Characteristics of Coating Films a. Growth of Microorganisms

PS polymers contain C, H, and O, among other elements as suitable nutrients for fungal and bacterial growth. When the PS polymer comes into contact with water, inevitably the growth of microorganisms already present in the water is stimulated, and bacterial colonies are formed. A serious problem in using such colonized polymer solutions as coating materials is caused by microbial bioparticles incorporated into layers of dried coating film which particles promote the rate of water transportation. The coating films become wet and fail as corrosion-protective coatings. Thus, adding an antimicrobial agent to the PE solution is needed to prevent the growth of microorganisms and the accumulation of water into the coating materials.

In the present invention, monomeric TSPI was employed as an antimicrobial agent. To assess its effectiveness on inhibiting microbial growth, 20 gram aqueous solutions having PS/TSPI ratios of 100/0, 99/1, and 97/3 were placed in culture flasks, and then left for two months at 25° C. in atmospheric environments. Subsequently, these solutions were deposited on aluminum substrate surfaces by dip-withdrawal coating methods, and then dried for 24 hours in a vacuum oven at 40° C. to transform them into solid films for SEM observations.

Figure 9A:
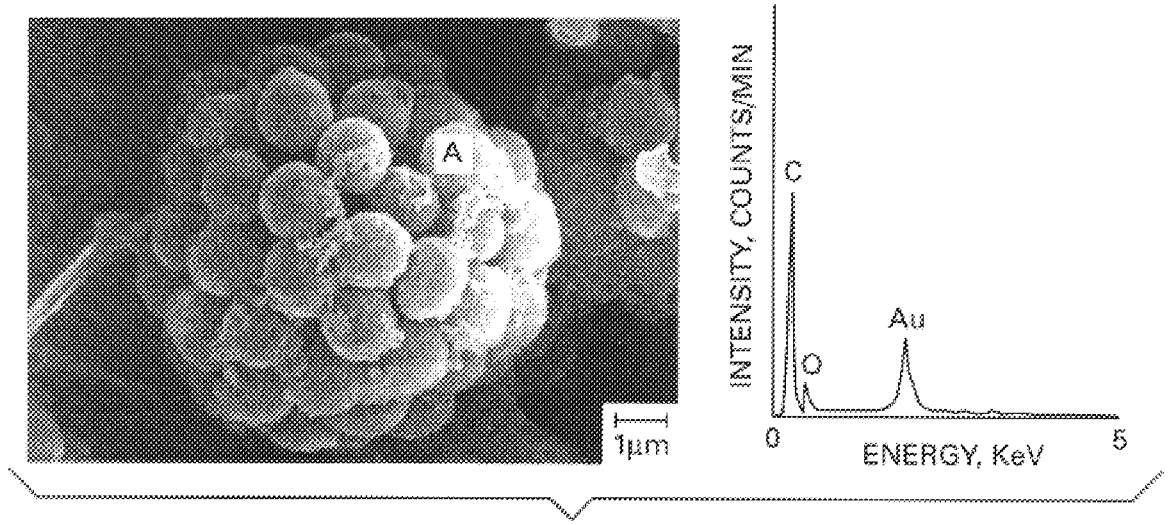
FIGS. 9(a) and 9(b) show SEM-EDX examination of coating surfaces derived from PE/TSPI solutions having ratios of 100/0 (top) and 97/3 (bottom) after leaving them for two months in culture flasks at 25° C.
Figure 9B:
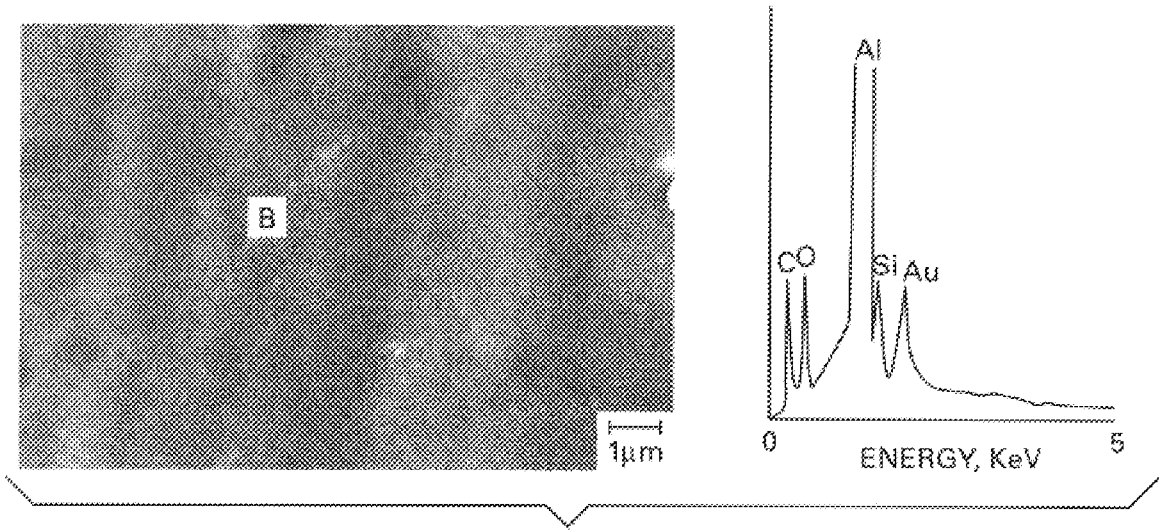

FIG. 9 shows SEM micrographs, coupled with EDX examinations of the surfaces of PE/TSPI coatings in a ratio of 100/0 at the top and 93/3 at the bottom. The SEM image from an unmodified PE coating disclosed a continuous coverage of extensive fungal clusters over the aluminum substrate. As expected, the EDX spectrum for the cluster denoted as site A showed the presence of only two organic elements, C and O, corresponding to microorganisms formed in the TSPI unmodified coating. There was no signal for the element aluminum which could have originated from the underlying substrate. Because EDX is useful for quantitative elemental analysis within a subsurface layer up to ≈1.5 $\mu$m thick, the microbial biofilms deposited on the aluminum appear to have been more than 1.5 $\mu$m thick. The element Au which was detected by EDX came from the Au coating film which had been deposited on the surface of the SEM sample. The SEM image of the 99/1 ratio PE/TSPI film is not shown in this figure; however, the morphology of its surface was similar to that of the 100/0 ratio film, revealing fungal clusters randomly distributed over the aluminum substrate.

A strikingly different feature was observed when PE was modified with a 3 wt % TSPI solution; there was no fungal growth in the films having a 97/3 ratio of PE/TSPI.

The EDX spectrum at site B had a dominant line of aluminum and moderate lines of C, O, Si, and Au. Because the aluminum and silicon elements belong to the substrate and TSPI, respectively, the thickness of this film is probably less than ≈1.5 $\mu$m. Nevertheless, this finding strongly suggested that the incorporation of a proper amount of TSPI as an antimicrobial agent prevented the growth of microorganisms in the PE solution.

To understand why the TSPI-incorporated PE solution causes microbial inertness, the chemical reaction products occurring between PE and TSPI in an aqueous medium were studied. Three solutions with PE/TSPI ratios of 99/1, 97/3, and 95/5, were poured into test tubes, and left for 24 hours at room temperature to yield a suspension of colloidal reaction products. The colloidal products were separated by filtration, and subsequently converted into a solid state by heating them for 20 hours in a $N_2$ saturated oven at 100° C.

Figure 10:
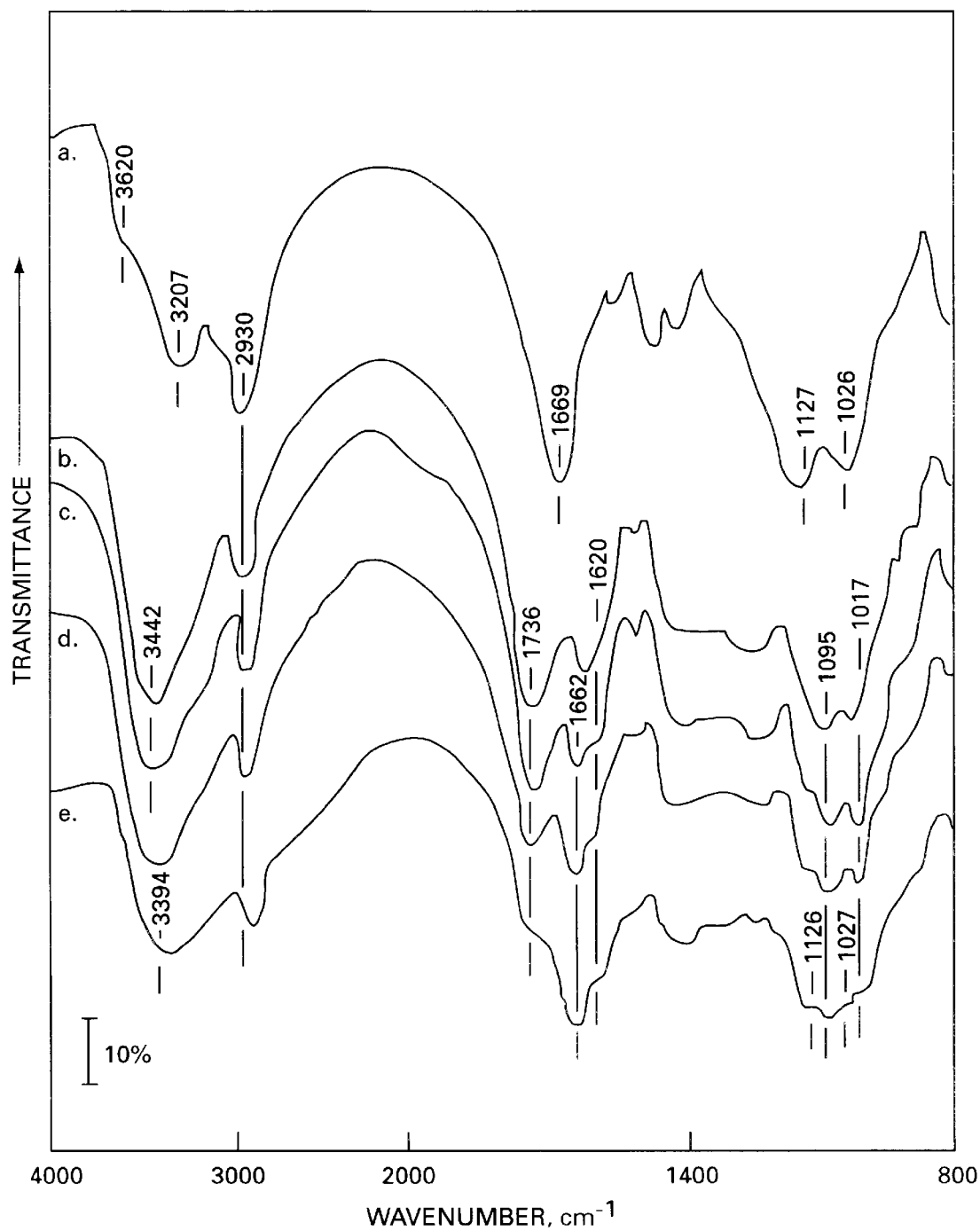
FIG. 10 illustrates FT-IR spectra for 100° C.-treated PE/TSPI ratio coatings as follows: 0/100 at (a), 100/0 at (b), 99/1 at (c), 97/3 at (d), and at 95/5 (e).

Finally, disks for FT-IR analysis, over the frequency ranges from 4000 to 800 cm$^{-1}$, were prepared by mixing 200 mg of KBr and 3 mg to 5 mg of powdered solid reaction product that had been crushed to a size of less than 0.074 mm. Also, IR spectra were taken of 100° C.-treated pure PE and TSPI as the reference samples. The results from these samples are shown in FIG. 10.

The hydrolysis of TSPI as catalyzed by HCl not only converted ethoxysilyl groups, Si—(OC$_2$H$_5$), into silanol groups, Si-OH, but also promoted the cleavage of the N-CH$_2$—linkage in TSPI, thereby generating the isolated imidazoline derivative,

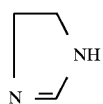

and the propylsilanol hydrolysate containing Cl-substituted end groups. The dehydrochlorinating and dehydrating condensation reactions between the hydrolysate finally induced the formation of polyorganosiloxane (POS) network structure. A typical spectrum 10(a) of 100°C.-treated bulk TSPI specimens reveals the formation of POS and imidazoline derivatives. The representative absorption bands can be interpreted as follows: O—H in the silanol groups at 3620 cm$^{-1}$; N—H in the imidazoline rings at 3287 cm$^{-1}$; C—H in the methylene chains and imidazoline at 2930 cm$^{-1}$; C=N in the imidazoline at 1669 cm$^{-1}$; Si—O—C in the Si-joined alkoxy groups at 1127 cm$^{-1}$; and, Si—O—Si in the polymeric siloxane at 1026 cm$^{-1}$. The spectrum of 100° C.-dried PE, 10(b), had six prominent peaks at band positions of 3442, 2930, 1736, 1620, 1095, and 1017 cm$^{-1}$.

The first four bands in the PE structure correspond to the OH, CH$_3$, C=O, and hydrogen-bonded C=O, respectively as is more specifically described in Bellamy, L. J., "The Infrared Spectra of Complex Molecules, vol., 3rd edition by Chapman & Hall, London, 1975. The bands at 1095 and 1017 cm$^{-1}$ are assignable to the C—O—C stretching vibration within the PE structure. When PE was modified with a 1 wt % TSPI solution (99/1 ratio PE/TSPI), the peculiar feature of its spectrum, shown in 10(c), was the development of a new frequency at band position of 1662 cm$^{-1}$, while the hydrogen-bonded C=O band at 1620 cm$^{-1}$ became a shoulder peak. This new band, corresponding to a shift in the high frequency site by 42 cm$^{-1}$ above that of hydrogen-bonded C=O, presumably reflected the formation of newly developed hydrogen bonds by interactions between silanol, OH in the TSPI hydrolysate, and C=O in the PE. This interpretation was supported by the fact that the signal intensity of the C=O band at 1736 cm$^{-1}$ decayed considerably with an increase in the concentration of TSPI. For instance, sample (e) as shown in FIG. 10 with a 95/5 PE/TSPI ratio showed that the peaks at 1662 and 1736 cm$^{-1}$ were converted into a predominant and a shoulder one, respectively. Thus, the rate of formation of hydrogen bonds between silanol and C=O appeared to be enhanced when highly concentrated TSPI was incorporated into PE. Conversely, a decrease in proportion of PE to TSPI markedly reduced the intensity of PE's OH band in the frequency range of 3442 to 3304 cm$^{-1}$. Of particular interest was the appearance of an absorption band at 1126 cm$^{-1}$ on the spectrum (e) of sample with a 95/5 ratio. Because this band revealed the presence of a Si—O—C linkage, one possible interpretation for the attenuation of the OH band implicated in the development of new frequency at 1126 cm$^{-1}$, was that the silanol groups not only had a chemical affinity with the C=O in PE to form the hydrogen bonds, but also favorably reacted with OH in PE to yield Si—O—C linkages. The latter pathway is explicable as a dehydrating condensation reaction between OH in silanol and OH in PE. The growth of a peak at 1027 cm$^{-1}$ in the spectrum of the 95/5 PE/TSPI sample, was assigned as originating from the siloxane band, Si—O—Si; this suggested that the POSs were grafted onto the PE polymer chain. The number of POS branches per PE chain and the length of POS grafts were related to the concentration of TSPI incorporated into the PE solution.

Assuming that all of functional OH and C=O groups in PE react with TSPI, a hypothetical structure of the PE copolymer with its POS grafts is illustrated below.

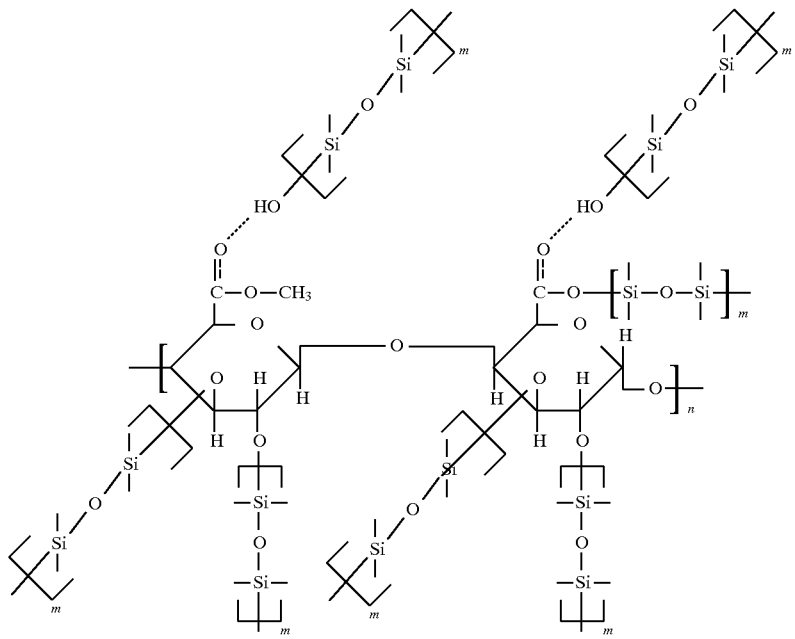

Without being bound by theory, it is believed that the reason for why TSPI-modified PE inhibits microbial growth is due to a combination of two factors. One factor is the chemical bonding between functional groups in PE and silanol groups in POS. The other factor is the alteration in molecular configuration of PE by grafting POS. The former factor not only serves in eliminating hydrophilic groups, such as OH and COOH in PE, but also contributes to an increase in the pH of the PE solution because of the decrease in numbers of COOH acid groups.

b. Thermal Characteristics

Figure 11:
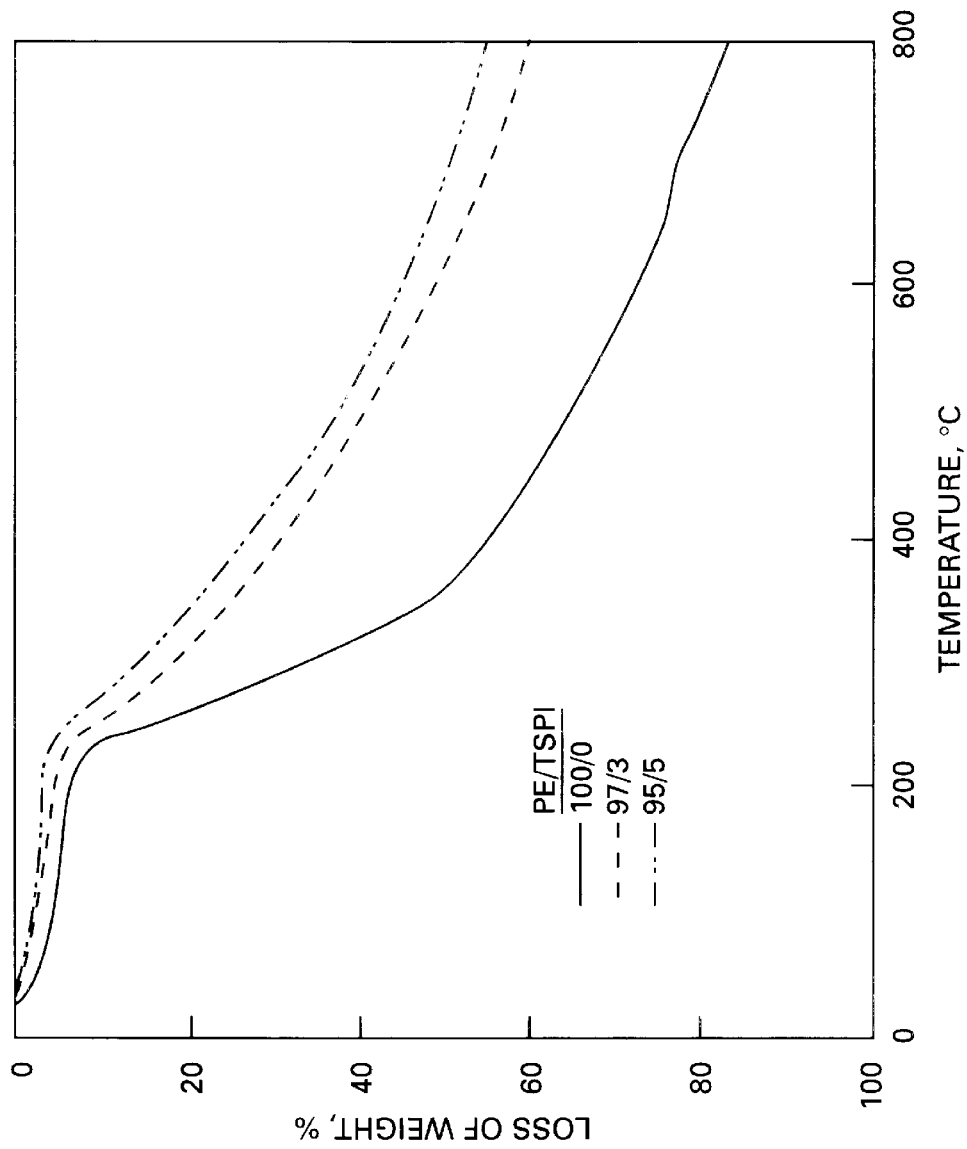
FIG. 11 illustrates TGA for the TSPI-modified and -unmodified PE polymers in air at a rate of 10° C./min.

Before surveying the ability of the PE copolymers with POS grafts to protect aluminum (Al) substrates from the NaCl-related corrosion, their thermal behavior using TGA was investigated. FIG. 11 illustrates TGA curves showing the thermal-decomposition characteristics of modified and unmodified PE polymers which had been pre-heated at 100° C. for 10 hours. All these samples displayed a slight weight loss in the initial temperature range from 25° C. to 150° C., which may reflect the liberation of moisture chemisorbed onto the copolymers. The curves indicate that the amount of liberated moisture depended on the PE/TSPI ratios; namely, the uptake of moisture decreased with decreasing ratio, suggesting that PE polymers modified with a large amount of TSPI were less susceptible to attack by moisture. The onset temperatures of decomposition were obtained by finding the intersection point of the two linear extrapolations. Thus, thermal decomposition of the unmodified PE polymers (100/0 ratio) began near 270° C. Similar onset temperature was recorded on the TGA curves of the TSPI-modified PE polymers with ratios of 97/3 and 95/15. However, the total weight loss at 400° C. was markedly reduced as the amount of TSPI was increased; weight loss in the 95/5 ratio polymer was only 25%, corresponding to a lowering more than twice that of the bulk PE polymer. Thus, the thermal stability of PE polymer was improved by incorporating a certain amount of TSPI. In other words, the increased number of POS branches and the extended length of POS grafts in the PE chain significantly improved the thermal stability of PE polymers.

c. Wettability of Coated Surfaces

In making water-impermeable coating films, the magnitude of the wettability of the film surfaces by water is among the most important factors governing a good protective performance. The degree of water-wettability of the TSPI-modified and unmodified PE film surfaces was estimated from the average value of the advancing contact angle on these surfaces. The films deposited on the aluminum surfaces were prepared by heating them in an oven for 2 hours at 50°–250° C.

Figure 12:
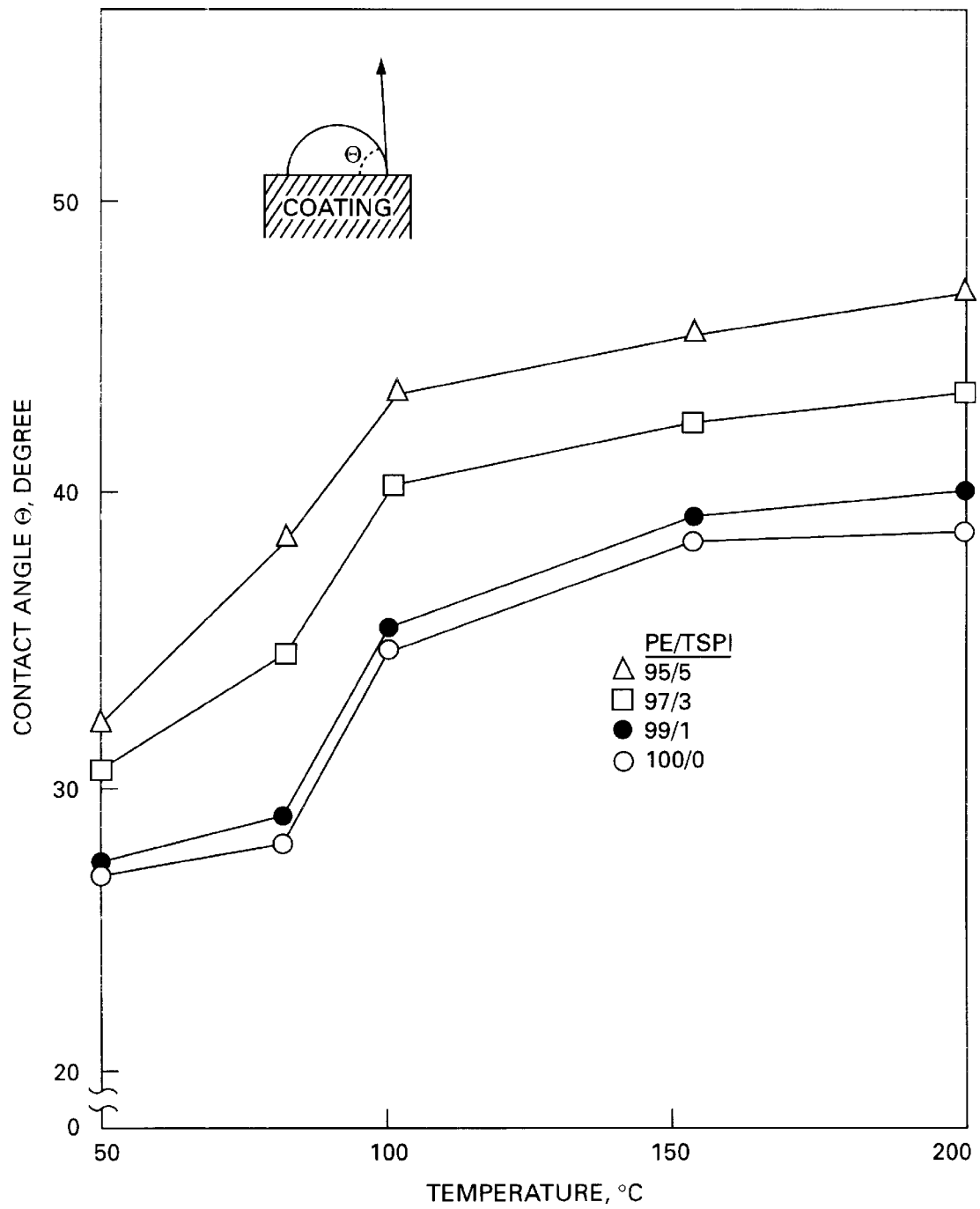
FIG. 12 shows changes in the contact angle of film surfaces made from films having various different PE/TSPI ratios as a function of temperature.

FIG. 12 depicts the changes in contact angle, $\theta$, as a function of the film-treating temperatures, for the 100/10, 99/1, 97/3, and 95/15 ratio PE/TSPI polymers. The resultant $\theta$-temperature curves demonstrated that the contact angle depends primarily on the PE/TSPI ratio and treatment temperature of the films; a high contact angle was observed in films with a low ratio of PE/TSPI treated at elevated temperatures. Because a high contact angle correlates with a lowering of wetting, the 200° C.-treated film surfaces with a 95/15 ratio had the least susceptibility to moisture. This finding strongly supported the characteristics previously discussed, namely, that modification of PE with TSPI removed hydrophilic OH and COOH groups in the PE. Thus, incorporating a large amount of TSPI into PE promoted the rate of dehydrating condensation reactions between the OH in PE and the silanol OH in TSPI, thereby increasing the number of POS branches per PE chain. In contrast, a further increase in temperature to 250° C. caused a drop in $\theta$ for all film surfaces. This enhancement in water-wetting behavior may be due to thermal decomposition of the film because the onset temperature for thermal decomposition for all these polymers is about 270° C.

d. The Interfacial Bond Structures and Reaction Products Formed at Interfaces Between Coatings and Metals The chemistry at interfaces between a coating and the substrate it coats is one of the important factors governing the ability of polymers to protect metals against corrosion. Several other investigators have reported that imidazole type compounds are effective in affording some corrosion protection to metals, such as copper, iron, and aluminum. The corrosion-inhibiting activity of this compound was due mainly to the formation of a water-insoluble imidazole complex with metals derived from the adsorption of imidazole rings onto metal oxide surfaces. See, for example Dugdale, I., et al., in Corrosion Science, 3, p. 69, 1963; Mayanna, S. M., et al., in Corrosion Science, 15, p. 627, 1975; Yoshida, S., et al., in Journal of Material Science, 78, p. 6960, 1983.

The complete coverage of the oxide surfaces by complex layers retarded the rate of cathodic reactions, known as oxygen-reduction reactions, thereby inhibiting corrosion of the metals. As described previously, the HCl-catalyzed hydrolysis of TSPI led to the isolation of the imidazoline derivative from TSPI. Thus, if the concept of other researchers is correct, the metal surfaces might have preferentially reacted with the imidazoline derivative to form water-insoluble complexes with metal, rather than with POS. XPS was employed to obtain this information.

Samples according to the present invention were prepared in the sequence described below. The aluminum substrate was dipped into a 97/3 ratio PE/TSPI solution, and then, the solution-covered aluminum was dried for 1 hour in an oven at 80° C. to form a water-soluble xerogel film. Most of the xerogel film was removed from the aluminum surface by immersing it in deionized water. Subsequently, the film-devoid aluminum side was dried for 1 hour in $N_2$ gas at 100° C. for XPS examination. An XPS survey scan of the Al side indicated the presence of four different atoms, Al, Si, C, and O, corresponding to $Al_{2p}$, $Si_{2p}$, $C_{ls}$, and $O_{ls}$ core-level excitation peaks. The alkali-cleaned Al surfaces not only have Al and O atoms attributed mainly to the formation of $Al_2O_3$, but also include elemental Si. Thus, Al, and some Si and O atoms originated from the substrates. Assuming that the Si, C, and O atoms are attributable to residual POS-grafted PE copolymer film adhering to the substrate, this film was thin enough to see the photoemission signal from the underlying Al substrate. XPS is commonly used to identify the chemical compositions and states for superficial layers at the penetrating depth of photoelectron, from 50 to 500 nm, suggesting that the thickness of such residual film may be no more than 500 nm. However, the peak for N element originating from N in the imidazoline derivatives was too weak to be detected in the $N_{ls}$ core-level region. Thus, although imidazoline may be adsorbed on metal surfaces, imidazoline complexes with metal were susceptible to dissolution in water. In contrast, POS grafts adsorpted to metals formed water-insoluble structures, indicating that the POS grafts could have had a strong affinity for the $Al_2O_3$ layers that were present at the outermost surface site of aluminum.

Figure 13:
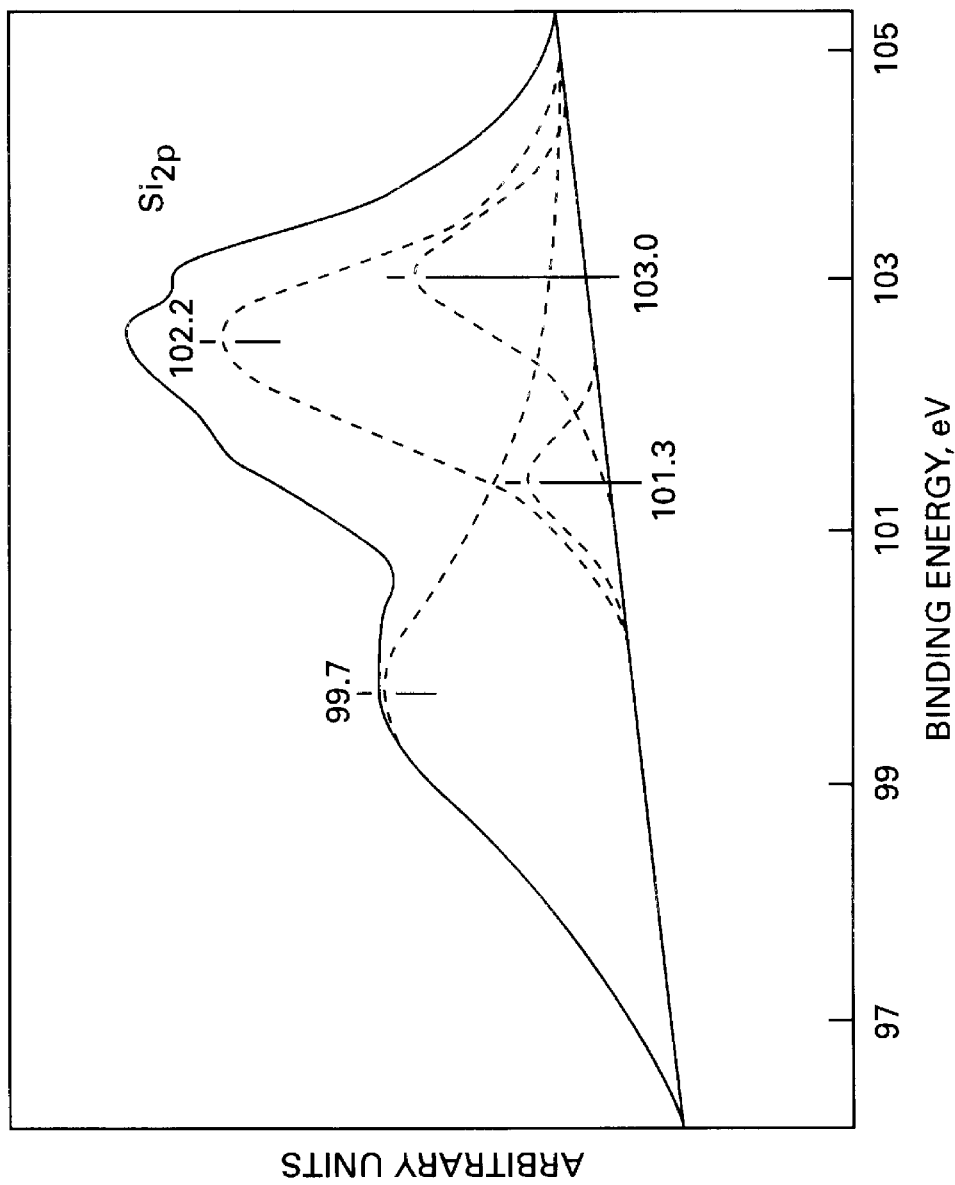
FIG. 13 shows XPS $Si_{2p}$ core-level spectrum for the 97/3 ratio PE/TSPI coating at interference with aluminum substrate.

XPS was used in order to understand the characteristics of the POS grafts and the role they played in promoting atomic linkages with $Al_2O_3$. The XPS $Si_{2p}$ region exciting at the film-$Al_2O_3$ interfaces is shown in FIG. 13. The deconvoluted curve for this sample revealed four Gaussian compounds at the BE position of 99.7, 101.3, 102.2, and 103.0 eV. According to Loreny, W. J., et al., in Corrosion Science, 21, p.647, 1981, the peak at 102.2 eV as the major line was assignable to the Si in the siloxane groups, Si—O—Si, and the secondary intense line at 99.7 eV originated from the elemental Si in the underlying aluminum substrate. The weakest peak at 101.3 eV as the minor component was due to the Si in the silanol groups, Si—OH. Of particular interest was the excitation of 103.0 eV line, belonging to the silicate groups. Considering that the silicate compounds were implicated in forming water-insoluble complexes consisting of Si, O, and metals, this interesting peak was assignable to the Si in the Si—O—metal linkages. Because the metal comes from the aluminum substrate, it was assumed that such a linkage, in terms of interfacial covalent oxane-bond structure, might be formed by interactions at interfaces between POS and $Al_2O_3$.

All the information described above was correlated directly with the results from the electrochemical impedance spectroscopy (EIS) for 100/0, 99/1, 97/3, and 95/5 ratio-PE/TSPI coated aluminum specimens as a function of film-treating temperatures up to 250° C. EIS curves for these specimens in a 0.5N NaCl solution at 25° C. were representative of the Bode-plot features (the absolute value of impedance, $|Z|$, ohm-$cm^2$ vs. frequency, Hz). Particular attention in the overall EIS curve was given to the impedance value as the element $|Z|$, which can be determined from the plateau in the Bode plot occurring at sufficiently low frequencies. The impedance of the uncoated bare aluminum substrate was $\approx 5.0 \times 10^3$ ohm-$cm^2$ at a frequency of 0.5 Hz.

Figure 14:
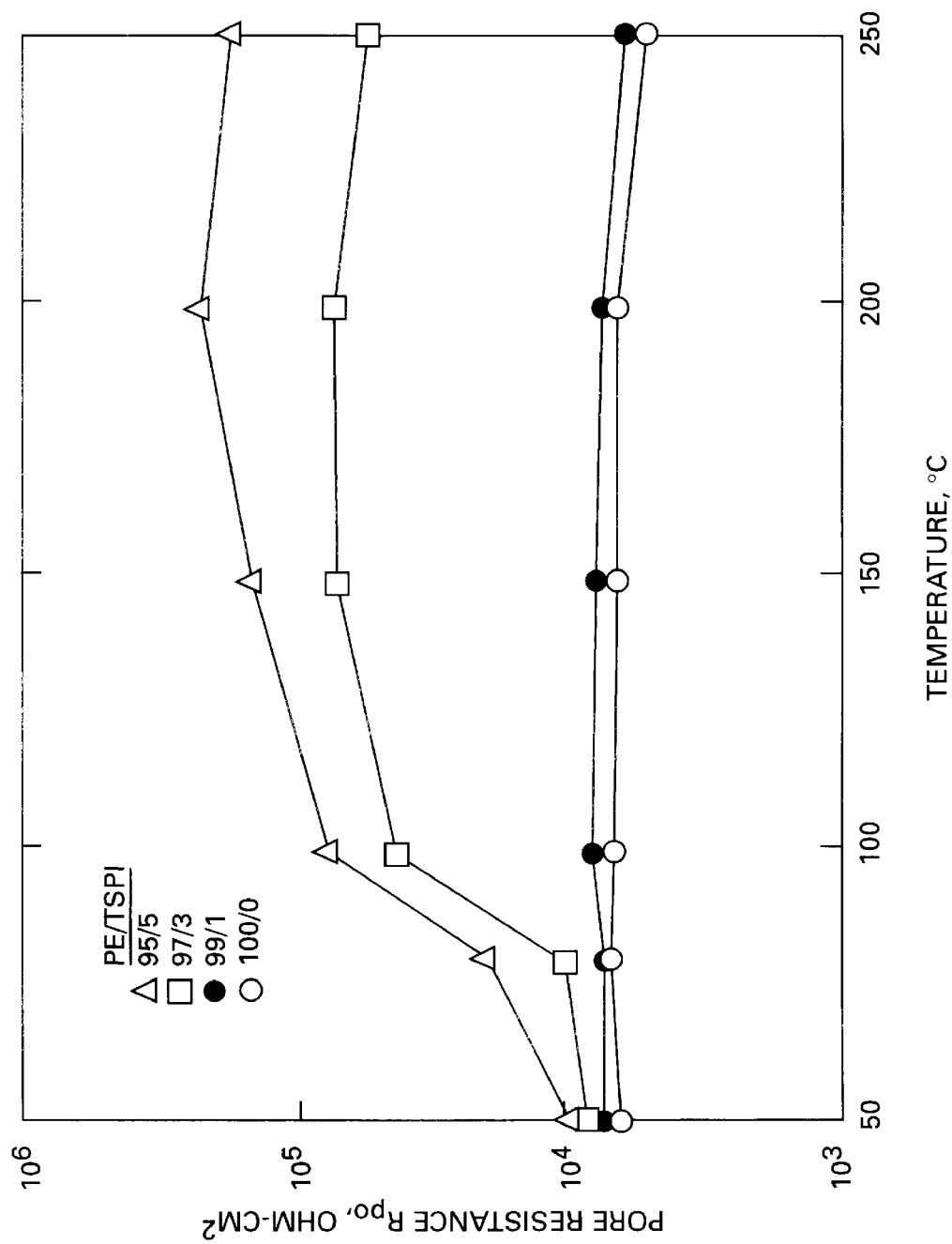
FIG. 14 shows changes in pore resistance, $R_{po}$, as a function of temperature for various PE/TSPI ratio coatings deposited on aluminum substrates.

Once the aluminum surfaces were coated with bulk PE and grafted PE copolymers, the impedance at the same frequency, in terms of the pore resistance, $R_{po}$, of the coatings, increased by some degree of magnitude over that of the substrate as shown in FIG. 14. For instance, the $R_{po}$ value of the 50° C.-treated bulk PE coating was somewhat higher than that of the bare aluminum. When PE was grafted with POS, the $R_{po}$ for the coating treated at the same temperature increased with the increased proportion of TSPI to PE. The $R_{po}$ values reflect the magnitude of ionic conductivity generated by the electrolyte passing through the coating layers; namely, a high value of $R_{po}$ corresponds to a low degree of penetration of electrolyte into the coating film. Comparing $R_{po}$ values, the effectiveness of PE/TSPI ratios in ensuring a low degree of penetration of electrolyte was in the following order: 95/5>97/3>99/1>100/0. In addition, an increase in treatment temperature, especially for the 95/5 and 97/3 PE/TSPI ratio coatings, contributed significantly to increasing the $R_{po}$ value. Thus, treatment at 200° C. increased $R_{po}$ by one or two orders of magnitude over that of the 50° C.-treated coatings. Temperature had little effect on the $R_{po}$ for the 100/0 and 99/1 ratio coatings. As expected, a temperature at 250° C. was too high to be employed for assembling the coating films because of the thermal degradation of PE polymers, thereby resulting in a decrease in $R_{po}$.

In conclusion, the major reason for the antimicrobial activity of TSPI was due to two factors: 1) chemical bonding between the functional groups, such as OH and C=O, in PE, and the silanol hydrolysate derived from hydrolysis of TSPI, and 2) grafting of polyorganosiloxane (POS), formed by dehydrating condensation reactions between neighboring silanols, into the PE polymer chain. Such a grafted copolymer structure was formed by the condensation reaction between silanol end groups in POS and OH groups in PE, and also by hydrogen bonding between silanol hydrogen and C=O oxygen. The formation of POS-grafted PE copolymers not only conferred thermal stability on the copolymer conformation, but also, they were less susceptible to moisture because hydrophilic groups, such as OH and COOH, had been removed from PE. Furthermore, the silanol end groups in the POS grafts favorably reacted with the $Al_2O_3$ at the metal's outermost surface side to form interfacial covalent oxane bonds in terms of a water-insoluble bonding structure.

EXAMPLE 3

To ascertain whether TSPI acted properly as an antimicrobial agent for other natural polymers, such as potato starch, amylopectin, and hydroxyethyl cellulose, the ability of TSPI-modified starch, amylopectin, and cellulose coatings to protect aluminum (Al) alloys against corrosion was examined.

In TSPI-starch systems, the coating films were deposited onto aluminum substrate surfaces in accordance with the following sequence: the alkali-cleaned aluminum substrates were dipped for a few seconds into mixed aqueous solutions consisting of 98 to 60 wt % TSPI solution (9.5 wt % starch dissolved in water at $\approx 90°$ C.) and 2 to 40 wt % TSPI solution (9.5 wt % TSPI, 3.8 wt % $CH_3OH$, 1.0 wt % HCl and 85.7 wt % water) at temperatures, ranging from 90° C. to 25° C. After dipping, the substrates were withdrawn and then dried for 10 to 300 minutes at temperatures of up to 200° C.

In TSPI-amylopectin systems, the alkali-cleaned aluminum substrates were dipped for a few seconds into mixed aqueous solutions of 0.2 to 2.5 wt % amylopectin dissolved in water at 80° C. and 2 to 40 wt % TSPI solution (9.5 wt % TSPI, 3.8 wt % $CH_3OH$, 1.0 wt % HCl and 85.7 wt % water) at temperatures, ranging from 80° C. to 25° C. After dipping, the substrates were withdrawn and then dried for 10 to 300 minutes at temperatures of up to 200° C.

In TSPI-cellulose systems, the alkali-cleaned aluminum substrates were dipped for a few seconds into mixed aqueous solutions of 0.2 to 2.5 wt % cellulose dissolved in water at 80° C. and 2 to 40 wt % TSPI solution (9.5 wt % TSPI, 3.8 wt % $CH_3OH$, 1.0 wt % HCl and 85.7 wt % water) at temperatures, ranging from 80° C. to 25° C. After dipping, the substrates were withdrawn and then dried for 10 to 300 minutes at temperatures of up to 200° C.

Regarding the corrosion protection of the aluminum alloy, the coating systems developed above were compared to conventional coating systems as shown in Table 4.

TABLE 4

| COATING | FILM THICKNESS | IMPEDANCE, OHM-$CM^2$ | SALT-SPRAY RESISTANCE, HR |
|---|---|---|---|
| Blank Al | — | $10^2$ | 24 |
| Anodic Oxide | $\approx 10$ µm | $10^3$–$10^4$ | $\approx 300$ |
| Cr-Conversion (Alodine 600) | Unknown | $10^4$ | $\approx 500$ |
| Polybutadiene | $\approx 8$ µm | $10^5$–$10^6$ | >2000 |
| Natural Polymers of Invention | 0.5–1.0 µm | $10^5$–$10^6$ | >1000 |

As illustrated in Table 4 above, the extent of such resistance to corrosion was far better than that of conventional anodic oxide and Cr-conversion coatings. Thus, TSPI-modified natural polymer coatings have great potential as substitutive materials for the Cr-incorporated coatings which are known to be environmentally hazardous.

We claim:

1. A polysaccharide graft polymer comprising a structure of Formula I or Formula II

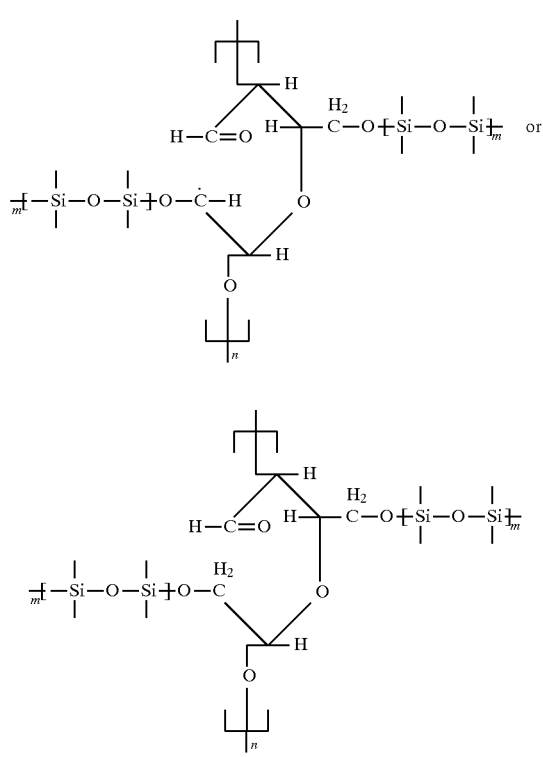

wherein the polysaccharide is selected from the group consisting of water dispersable starches, cellulose, cellulose esters or cellulose ethers, the segment is provided by an antimicrobial agent selected from the group consisting of halogen substituted silanes, N[3-(triethoxysilyl)-propyl]-4,5-dihydroimidazole, β-trimethoxysilylethyl-2-pyridine, β-trimethoxyxilyethyl-4-pyridine, 2-[2-trichlorosilyl)ethyl]pyridine, and 4-[2-((trichlorosilyl)ethyl]pyridine], and m and n are ≧500.

2. A method of making a polysaccharide polymer having a structure of Formula I or Formula II

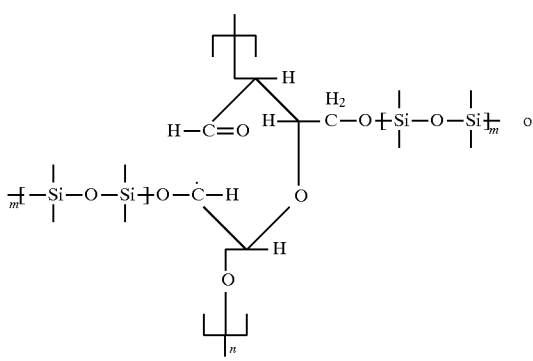

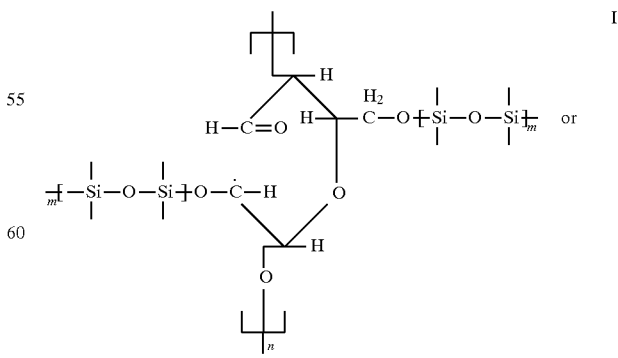

which comprises reacting a polysaccharide selected from a group consisting of water dispersable starches, cellulose, cellulose esters and cellulose ethers with an antimicrobial agent selected from the group consisting of halogen substituted silanes, N[3-(triethoxysilyl)-propyl]-4,5-dihydroimidazole, β-trimethoxysilylethyl-2-pyridine, β-trimethoxyxilylethyl-4-pyridine, 2-[2-trichlorosilyl)ethyl]pyridine, and 4-[2-(trichlorosilyl)ethyl]pyridine, under conditions of heat catalyzed dehydrating condensation.

3. The method of claim 2 wherein said polysaccharide source and said antimicrobial agent are colloidal aqueous solutions.

4. The method of claim 2, wherein said reaction occurs from about 50° C. to about 250° C.

5. The method of claim 2, wherein said polysaccharide source is selected from the group consisting of water dispersible starches and cellulosics.

6. The method of claim 2 wherein said polysaccharide source is from about 60 wt % to about 98 wt % and said antibacterial agent is from about 2 wt % to about 40 wt %.

7. The polymer of claim 1, wherein said halogen substituted silane is selected from the group consisting of: 3-bromopropyltrimethoxysilane; 3-iodopropyltrimethoxysilane; (3,3,3-trifluoropropyl)trimethoxysilane; (3,3,3-trifluoropropyl)triethoxysilane; tridecafluoro-1,1,2,2-tetrahydrooctyl-1-triethoxysilane.

8. The method of claim 2, wherein said halogen substituted silane is selected from the group consisting of: 3-bromopropyltrimethoxysilane; 3-iodopropyltrimethoxysilane; (3,3,3-trifluoropropyl)trimethoxysilane; (3,3,3-trifluoropropyl)triethoxysilane; tridecafluoro-1,1,2,2-tetrahydrooctyl-1-triethoxysilane.

9. A corrosion resistant coating having antimicrobial properties which comprises a polysaccharide graft polymer having a structure of Formula I or Formula II

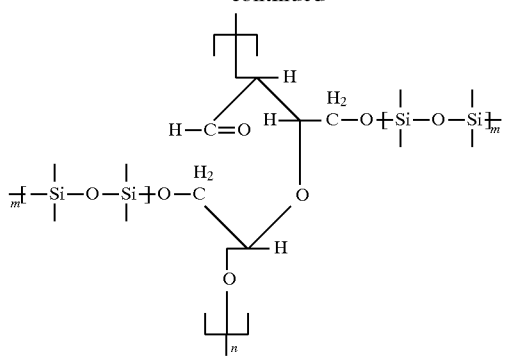

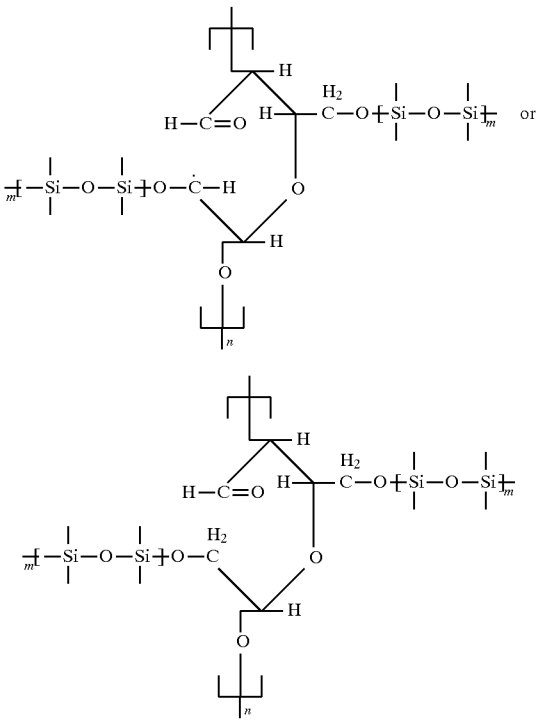

wherein the polysaccharide is selected from the group consisting of water dispersable starches, cellulose, cellulose esters or cellulose ethers, the segment is provided by an antimicrobial agent selected from the group consisting of halogen substituted silanes, N[3-(triethoxysilyl)-propyl]-4,5-dihydroimidazole, β-trimethoxysilylethyl-2-pyridine, β-trimethoxyxilylethyl-4-pyridine, 2-[2-trichlorosilyl)ethyl]pyridine, and 4-[2-(trichlorosilyl)ethyl]pyridine], and m and n are ≧500.

10. The coating of claim 9, wherein said halogen substituted silane is selected from the group consisting of: 3-bromopropyltrimethoxysilane; 3-iodopropyltrimethoxysilane; (3,3,3-trifluoropropyl)trimethoxysilane; (3,3,3-trifluoropropyl)triethoxysilane; tridecafluoro-1,1,2,2-terahydrooctyl-1-1-triethoxysilane.

11. A method of rendering a metallic surface of a substrate resistant to corrosion which comprises:

coating a metallic surface of a substrate with a coating including a polysaccharide graft polymer having the structure of Formula I or Formula II wherein the polysaccharide is selected from the group consisting of water dispersable starches, cellulose, cellulose esters or cellulose ethers, the segment is provided by an antimicrobial agent selected from the group consisting of halogen substituted silanes, N[3-(triethoxysilyl)-propyl]-4,5-dihydroimidazole, β-trimethoxysilylethyl-2-pyridine, β-trimethoxysilylethyl-4-pyridine, 2-[2-trichlorosilyl)ethyl]pyridine, and 4-[2-(trichlorosilyl)ethyl]pyridine], and m and n are ≧500.

12. The method of claim 11, wherein said halogen substituted silane is selected from the group consisting of: 3-bromopropyltrimethoxysilane; 3-iodopropyltrimethoxysilane; (3,3,3-trifluoropropyl)trimethoxysilane; (3,3,3-trifluoropropyl)triethoxysilane; tridecafluoro-1,1,2,2-tetrahydrooctyl-1-triethoxysilane.

* * * * *